(12) United States Patent
Krohn et al.

(10) Patent No.: US 7,217,806 B1
(45) Date of Patent: May 15, 2007

(54) GENE DEFECTIVE IN APECED AND ITS USE

(75) Inventors: Kai Krohn, Salmentaantie (FI); Maarit Heino, Kaskitie (FI); Pärt Peterson, Kaskitie (FI); Hamish Scott, Brunswick (AU); Stylianos Antonarakis, Geneva (CH); Maria Lalioti, Birmingham (GB); Nobuyoshi Shimizu, Sakura (JP); Jun Kudoh, Tokyo (JP)

(73) Assignee: Finnish Immunotechnology Ltd., Tampere (FI)

( * ) Notice: Subject to any disclaimer, the term of this patent is extended or adjusted under 35 U.S.C. 154(b) by 0 days.

(21) Appl. No.: 09/508,658

(22) PCT Filed: Sep. 23, 1998

(86) PCT No.: PCT/FI98/00749

§ 371 (c)(1),
(2), (4) Date: Nov. 3, 2000

(87) PCT Pub. No.: WO99/15559

PCT Pub. Date: Apr. 1, 1999

(30) Foreign Application Priority Data

Sep. 23, 1997 (FI) ..................................... 973762

(51) Int. Cl.
C07H 21/02 (2006.01)
C07H 21/04 (2006.01)
C07K 1/00 (2006.01)
C07K 14/00 (2006.01)
C07K 17/00 (2006.01)
C12Q 1/68 (2006.01)

(52) U.S. Cl. ..................................... 536/23.1; 536/23.5

(58) Field of Classification Search ............... 536/23.1, 536/24.3
See application file for complete search history.

(56) References Cited

U.S. PATENT DOCUMENTS 5,474,796 A * 12/1995 Brennan ..................... 427/2.13
6,951,928 B1 * 10/2005 Peltonen et al. ........... 536/23.1

FOREIGN PATENT DOCUMENTS

WO 9708201 3/1997
WO 9717437 5/1997

OTHER PUBLICATIONS

Kim et al; PNAS, vol. 93, pp. 15299-15304, 1996.*
Su et al; Current Opinion in Immunology, vol. 16, pp. 746-752, 2004.*
Aaltonen et al; Nature Genetics, vol. 17, pp. 399-403, 1997.*
Nagamine, K., et al. "Isolation of cDNA for a Novel Human Protein KNP-I . . . "*Biochemical and Biophysical Research Communications*, vol. 225, No. 1218 (1996) pp. 608-616.

(Continued)

*Primary Examiner*—Jehanne Sitton
(74) *Attorney, Agent, or Firm*—Ladas & Parry LLP

(57) ABSTRACT

The present invention relates to a novel gene, a novel protein encoded by said gene, a mutated form of the gene and to diagnostic and therapeutic uses of the gene or a mutated form thereof. More specifically, the present invention relates to a novel gene defective in autoimmune polyendocrinopathy syndrome type I (APS I), also called autoimmune polyendocrinopathy-candidiasis-ectodermal dystrophy (APECED) (MIM No. 240,300).

3 Claims, 10 Drawing Sheets

OTHER PUBLICATIONS

Bjorses, P., et al. "Genetic Homogeneity of Autoimmune Polyglandular Disease Type I" *American Journal of Human Genetics*, vol. 59, (1996) pp. 879-886.

Bjorses, P., et al. *Pediatric Research*, 41, (4osa 2) (1997) pp. 65A.

Kudoh, J., et al. "Localization of 16 Exons to a 450-kb Region . . . " *DNA Research*, vol. 4 (1997) pp. 45-52.

Jansen, E., et al. "The NNP-1 Gene (D2152056E), Which Encodes a Novel Nuclear . . . " *Genomics*, vol. 42 (1997) pp. 336-341.

Scott, H., et al. "Isolation of a human gene (HES1) with homology . . . " *Human Genetics* vol. 99, (1997) pp. 616-623.

Aaltonen, J., et al. "High-Resolution Physical and Transcriptional Mapping . . . " *Genome Research*, vol. 7, (1997) pp. 820-829.

Aaltonen, J., et al. "An Autoimmune Disease, APECED, caused by mutations . . . " *Nature Genetics*, vol. 17, (Nov. 1997) pp. 399-403.

Kentaro Nagamine, et al., "Positional cloning of the APECED gene", Nature Genetics vol. 17, Dec. 1997, pp. 393-398.

* cited by examiner

```
(SEQ ID NO: 37) AIR-1 : 299  CAVCRDGGELICCDGCPRAFHLACLSPPLREIPSGTWRCSSC  340
(SEQ ID NO: 38) AIR-1 : 434  .G..G..TDVLR.TH.AA...WR.HF.AGTSR.GTGL..R..  475
(SEQ ID NO: 39) Mi-2  : 373  .E..QQ...I.L..T....Y.MV..D.DMEKA.E.K.S.PH.  414
(SEQ ID NO: 40) Mi-2  : 452  .R..K..........T..SSY.IH..N...P...N.E.L.PR.  493
(SEQ ID NO: 41) TIF1  : 791  ....QN.........EK..KV...S.HV.T.TNF...E.I.TF.  832
                consensus    C  C         C  C           H  C                C  C
```

FIG. 5

GENE DEFECTIVE IN APECED AND ITS USE

FIELD OF THE INVENTION

The present invention relates to a novel gene, a novel protein encoded by said gene, a mutated form of the gene and to diagnostic and therapeutic uses of the gene or a mutated form thereof. More specifically, the present invention relates to a novel gene defective in autoimmune polyendocrinopathy syndrome type I (APS I), also called autoimmune polyendocrinopathy-candidiasis-ectodermal dystrophy (APECED) (MIM No. 240,300).

BACKGROUND

Autoimmune polyglandular syndrome type I (APS I), also known as autoimmune polyendocrinopathy-candidiasis-ectodermal dystrophy (APECED), is a rare recessively inherited disease (MIM No. 240,300) that is more prevalent among certain isolated populations, such as Finnish, Sardinian and Iranian Jewish populations. The incidence of the disease among the Finns and the Iranian Jews is estimated to be 1:25000 and 1:9000, respectively, whereas only few cases in other parts of the world are found each year.

APECED is one of the two major autoimmune polyendocrinopathy syndromes. The causing factor of APECED has not yet been identified. The syndrome is characterized by lack of tolerance to numerous self-antigens and can therefore be considered as a prototype of organ-specific autoimmune diseases. In APECED, the patient develops chronic mucocutaneous candidiasis soon after birth, and later several organ-specific autoimmune diseases, mainly hypoparathyreoidism, Addison's disease, chronic atrophic gastritis with or without pernicious anemia, and in puberty gonadal dysfunction occur [Ahonen P, Clin. Genet. 27 (1985) 535–542]. An accepted criterion for diagnosis of APECED is the presence of at least two of the three main symptoms, Addison's disease, hypoparathyroidism and candidiasis, in patients [Neufeld, M. et al., Medicine 60 (1981) 355–362]. Immunologically, the major findings are the presence of high-titer serum autoantibodies against the effected organs, antibodies against *Candida albicans*, and low or lacking T-cell responses toward candidal antigens [Blizzard, R. M. and Kyle M., J. Clin. Invest. 42 (1963) 1653–1660; Arulanantham, K. et al., New Eng. J. Med. 300 (1979) 164–168; Krohn, K. et al., Lancet 339 (1992) 770–773; Uibo R. et al., J. Clin. Endocrinol. Metab. 78 (1994) 323–328]. The disease usually occurs in childhood, but new tissue specific symptoms may appear throughout life [Ahonen, P. et al., New Engl. J. Med. 322 (1990) 1829–1836]. APECED is not associated with a particular HLA haplotype, and both males and females are equally affected consistant with the autosomal recessive mode of inheritance.

The locus for the APECED gene has been mapped to chromosome 21q22.3 between gene markers D21S49 and D21S171 based on linkage analysis of Finnish families [Aaltonen, J. et al., Nature Genet. 8 (1994) 83–87]. Recently, Börses et al. reported a maximum LOD score of 10.23 with marker D21S1912 just proximal to the gene PFKL, and thus by linkage disequilibrium studies the critical region for APECED can be considered to be less than 500 kb between markers D21S1912 and D21S171. Locus heterogeneity was not revealed by linkage analysis of non-Finnish families [Björses, P. et al., Am. J. Hum. Genet. 59 (1996) 879–886].

For the APECED gene, the name "autoimmune regulator" or "AIRE" has been adopted by the scientific community after the priority date of the present application. Similarly the protein encoded by the AIRE gene is now called the "AIRE protein".

Physical maps of human chromosome 21q22.3 have been developed using YACs, and bacterial based large insert cloning vectors [Chumakov et al., Nature 359 (1992) 380; Stone et al., Genome Res. 6 (1996) 218], and many laboratories have contributed to the construction of a transcription map of the whole chromosome and 21q22.3 in particular [Chen et al., Genome Res. 6 (1996) 747–760; Yaspo et al., Hum. Mol. Genet. 4 (1995) 1291–1304]. Numerous trapped exons from chromosome 21 specific cosmids and also physical contigs from the APECED critical region have been identified and partially characterized. In addition, a number of ESTs from the international human genome project have been mapped to the APECED critical region.

Recently, as part of the international efforts of generating the entire sequence of human chromosome 21 and international agreements on the immediate availability of this type of sequence data, the partial sequence of the APECED gene critical region was made available in GenBank by the Stanford Human Genome Center which is currently carrying out the sequencing of 1.0 Mb around the critical region of the APECED gene.

However, the precise location and the sequence of the APECED gene and the nature of the gene product have not so far been clarified. Thus at present the diagnosis of APECED is based mainly on developed clinical symptoms and typical clinical findings, e.g. the presence of autoantibodies against adrenal cortex or steroidogenic enzymes P450c17 and/or P450scc. The linkage analysis is seldom used. Further, means for natal or presymptomatic diagnosis of the disease are not easily available, since the linkage analysis provides only an indirect data through known gene markers and requires samples from several family members in several generations. Additionally, the linkage analysis is tedious and can be performed only in specialized laboratories by highly-skilled personnel.

Also the mapping of the carriers of the disease gene is presently based on the linkage analysis and thus not readily available.

SUMMARY OF THE INVENTION

We have now identified a novel gene encoding a novel zinc finger protein, designated as autoimmune regulator 1 or AIR-1, which is mutated in APECED. The novel gene and protein allow further development of the diagnosis and therapy of diseases related to immune maturation and regulation of immune response towards self and nonself, such as APECED.

The object of the invention is to provide means which are useful in a diagnostic method and a gene therapeutic method in the diagnosis and treatment of diseases related to immune maturation and regulation of immune response towards self and nonself, such as APECED.

Another object of the invention is to provide a novel method for the diagnosis of diseases related to immune maturation and regulation of immune response towards self and nonself, such as APECED, including the pre- and postnatal diagnosis and the mapping of the carriers, the method being easy and reliable to perform.

The present invention relates to an isolated DNA sequence comprising the sequence id. no. 1 or a functional fragment or variant thereof, or a functionally equivalent isolated DNA sequence hybridizable thereto, the DNA sequence being associated with diseases related to immune maturation and regulation of immune response towards self and nonself, such as APECED. Preferably said isolated DNA sequence includes a gene defect responsible for APECED.

The present invention also relates to a protein comprising the amino acid sequence id. no. 2 or a functionally equivalent fragment or variant thereof, the protein being associated with diseases related to immune maturation and regulation of immune response towards self and nonself, such as APECED. Said protein has distinct structural motifs, including the PHD finger motif (PHD), the LXXLL motif (L), proline-rich region (PRR), and cystein-rich region (CRR).

The present invention further relates to a method for the diagnosis of diseases related to immune maturation and regulation of immune response towards self and nonself, such as APECED, comprising detecting in a biological specimen the presence of a DNA sequence comprising the sequence id. no. 1 or a functional fragment or variant thereof, or a functionally equivalent DNA-sequence hybridizable thereto, the DNA sequence being associated with diseases related to immune maturation and regulation of immune response towards self and nonself, such as APECED.

The present invention further relates to the use of the above-identified DNA-sequences in the diagnosis of diseases related to immune maturation and regulation of immune response towards self and nonself, such as APECED.

The present invention further relates to a method for the diagnosis of diseases related to immune maturation and regulation of immune response towards self and nonself, such as APECED, comprising detecting in a biological specimen the presence or the absence of a protein comprising the sequence id. no. 2 or a functionally equivalent fragment thereof, the protein being associated with diseases related to immune maturation and regulation of immune response towards self and nonself, such as APECED.

The present invention further relates to the use of the above-identified protein or a functionally equivalent fragment thereof in the diagnosis of diseases related to immune maturation and regulation of immune response towards self and nonself, such as APECED.

The present invention further relates to the use of the above-identified DNA sequences in gene therapy or for the preparation of a pharmaceutical preparation useful in a gene therapy method of diseases related to immune maturation and regulation of immune response towards self and nonself, such as APECED.

BRIEF DESCRIPTION OF THE DRAWINGS

FIG. 5 shows an amino acid sequence alignment for the PHD finger motif of AIR-1 (SEQ ID NO:38), Mi-2 (SEQ ID NO:39 and SEQ ID NO:40), and TIF1 (SEQ ID NO:41). The consensus amino acid residues conserved in the PHD finger motif is indicated by the bold letters underneath. The residues that are identical with AIR-1 (aa 299–340) (SEQ ID NO: 37) are shown by the dots. GenBank accession nos. of Mi-2 and TIF1 are X86691 and AF009353, respectively.

FIG. 7 shows the expression of the APECED mRNA (7A) or the AIR protein (7B, 7C and 7D) demonstrated by in situ hybridization (7A) or by immunohistochemistry (7B, 7C and 7D).

FIG. 8 shows the phenotypic characterization of the APECED reactive cells in thymus by double-immunofluorescence. The AIR protein is seen as red colour in the nuclei, forming typical speckled pattern with nuclear dots.

DETAILED DESCRIPTION OF THE INVENTION

Figure 1:
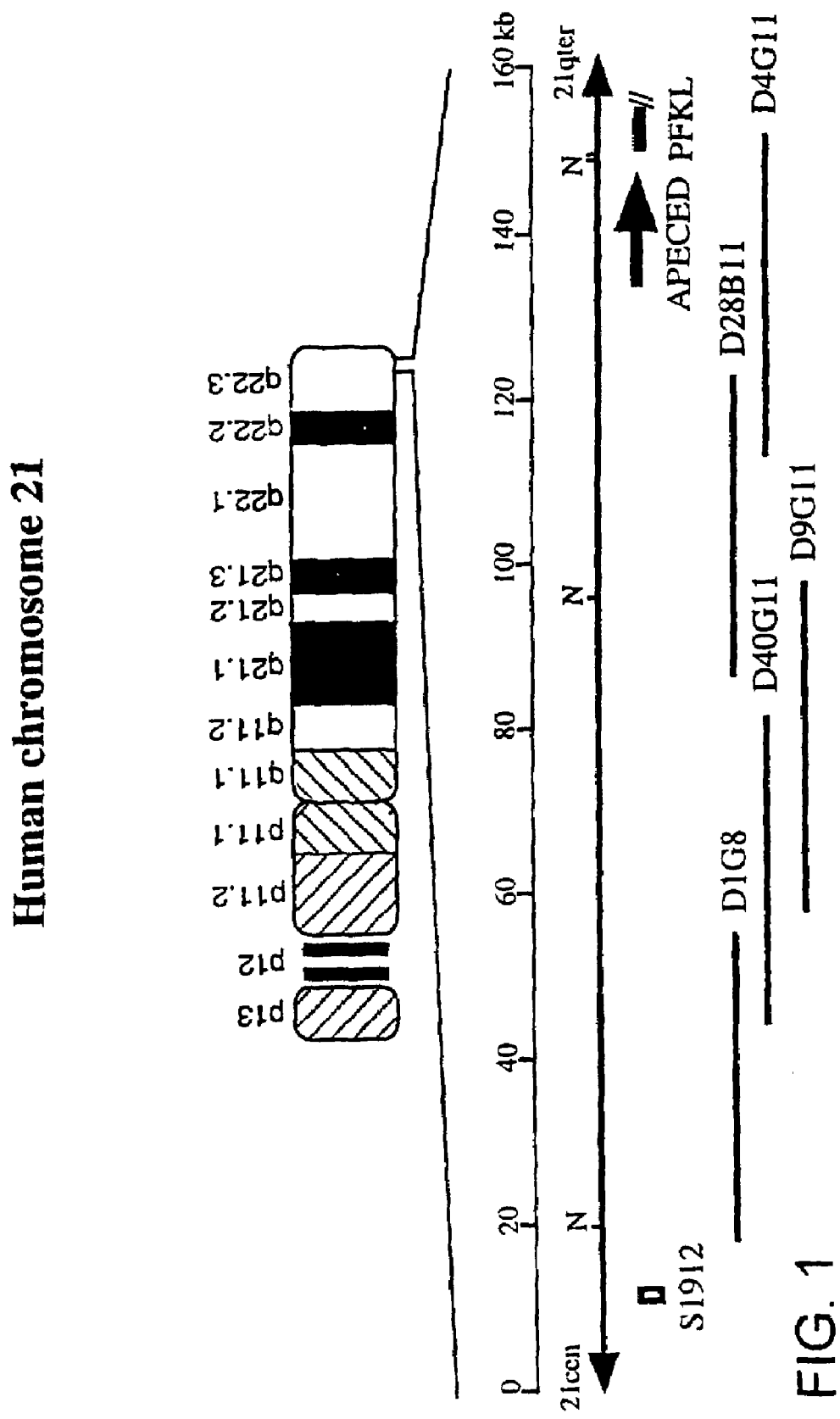
FIG. 1 shows a physical map of the APECED gene locus in the chromosome 21q22.3. Cosmids D1G8, D40G11, D9G11, D28B11, and D4G11, overlapping clones used for the genomic sequencing [Kudoh, J. et al., DNA Res. 4 (1997) 45–52] are indicated by horizontal lines. The APECED gene located just proximal to the 5' end of the neighboring gene PFKL is indicated by a solid arrow. N indicates NotI sites. DNA marker D21S1912 is shown as open box.

The present invention is based on studies aiming for the identification and characterization of the gene defect in APECED. In the sequence studies, a cosmid/BAC (bacterial artificial chromosome) contig of 520 kb covering four gene markers D21S1460-D21S1912-PFKL-D21S154 [Kudoh, J. et al., DNA Res. 4 (1997) 45–52] was constructed, and genomic sequencing in this region was performed [Kawasaki, K. et al., Genome Res. 7 (1997) 250–261]. From this genomic sequence information the distance between D21S1912 and PFKL was determined to be approximately 140 kb (FIG. 1).

Figure 2:
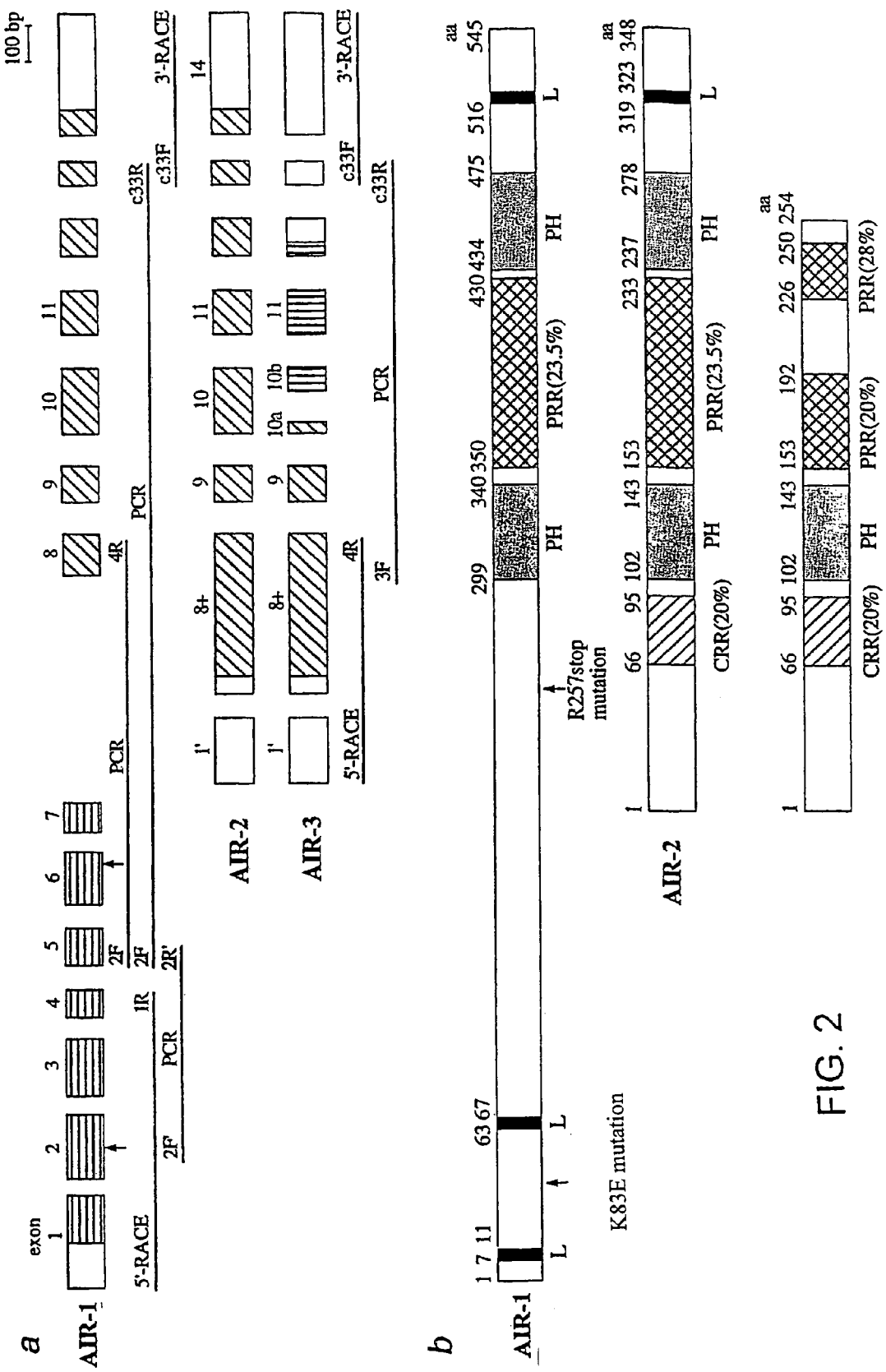
FIG. 2 shows the structures of the APECED gene and AIR proteins. (A) Cloning strategy of APECED cDNAs and the order of the exons in the APECED gene. DNA fragments amplified by PCR and 3'- and 5'-RACE are indicated by the lines. Exon 1' is the 5'-noncoding exon of the AIR-2 and AIR-3. An additional alternative splicing of AIR-3 in exon 10, resulting in an amino acid change in its downstream, is indicated by vertical lines. Each exon, except exon 1', is bordered by the common splice site consensus sequence, ag:gt. Mutations in the exon 2 and exon 6 are indicated by the arrows. (B) Schematic presentation of the three AIR proteins showing distinct structural motifs, including the PHD finger motif (PHD), the LXXLL motif (L), proline-rich region (PRR), and cystein-rich region (CRR).

Using a computer program, such as GRAIL and GENSCAN [Uberbacher, E. C. and Mural, R. J., Proc. Natl. Acad. Sci. USA 88 (1991) 11261–11265; Burge, C. and Karlin, S., J. Mol. Biol. 268 (1997) 78–94], gene screening in the partial sequencing data within this region was performed. GENSCAN predicted several genes between D21S1912 and PFKL. One of these genes located just proximal to the PFKL gene contained the previously trapped exon HC21EXc33 [Kudoh, J. et al., DNA Res. 4 (1997) 45–52] or MDC04M06 [Chen, H. et al., Genome Res. 6 (1996) 747–760]. A set of primers for polymerase chain reaction (PCR) was then designed from the predicted exons. The PCR screening of various cDNA libraries using these primers allowed the isolation of a cDNA clone containing the exon HC21EXc33 (exon 13) from the thymus cDNA library (FIG. 2A).

A 3'-rapid amplification of cDNA ends (3'-RACE) and 5'-RACE using Marathon™ cDNA Amplification Kit (Clontech Laboratories Inc, California, USA) according to manufacturer's protocol from the thymus cDNA library was performed using a primer c33F (sequence id. no. 7) and a primer 1R (sequence id. no. 8), respectively.

Sequencing analysis revealed a unique sequence of 2027 bp in overlapping PCR products that contains a 1635-bp open reading frame (ORF) from methionine at nt 128 to a TAG stop codon at nt 1763 encoding a predicted novel protein designated AIR-1, for autoimmune regulator 1. AIR-1 encodes a protein of 545 amino acids with a predicted isoelectric point of 7.32 and a calculated molecular mass of 57,723 (FIG. 2B).

A 5'-RACE from the thymus cDNA using a primer 4R (sequence id. no. 9) resulted in an alternatively spliced product. Furthermore, two types of the cDNA clones were amplified with a primer pair 3F/c33R (sequence id. no. 10/sequence id. no. 11) and these clones encode for AIR-2 and AIR-3 proteins, sequence id. no. 4 and sequence id. no. 6, respectively (FIG. 2A) (sequence id. no. 3 and sequence id. no. 5). The AIR-2 and AIR-3 proteins consist of 348 and 254 amino acids, respectively (FIG. 2B). These results suggest that the APECED gene is transcribed as at least three types of mRNA by alternative splicing and/or use of an alternative 5' exon within the gene. RT-PCR analysis [Griffin, H. G. and Griffin, A. M., PCR Technology. Current Innovations, CRC Press, 1994] revealed that the AIR-1 transcript is also expressed in fetal liver (data not shown).

Figure 3:
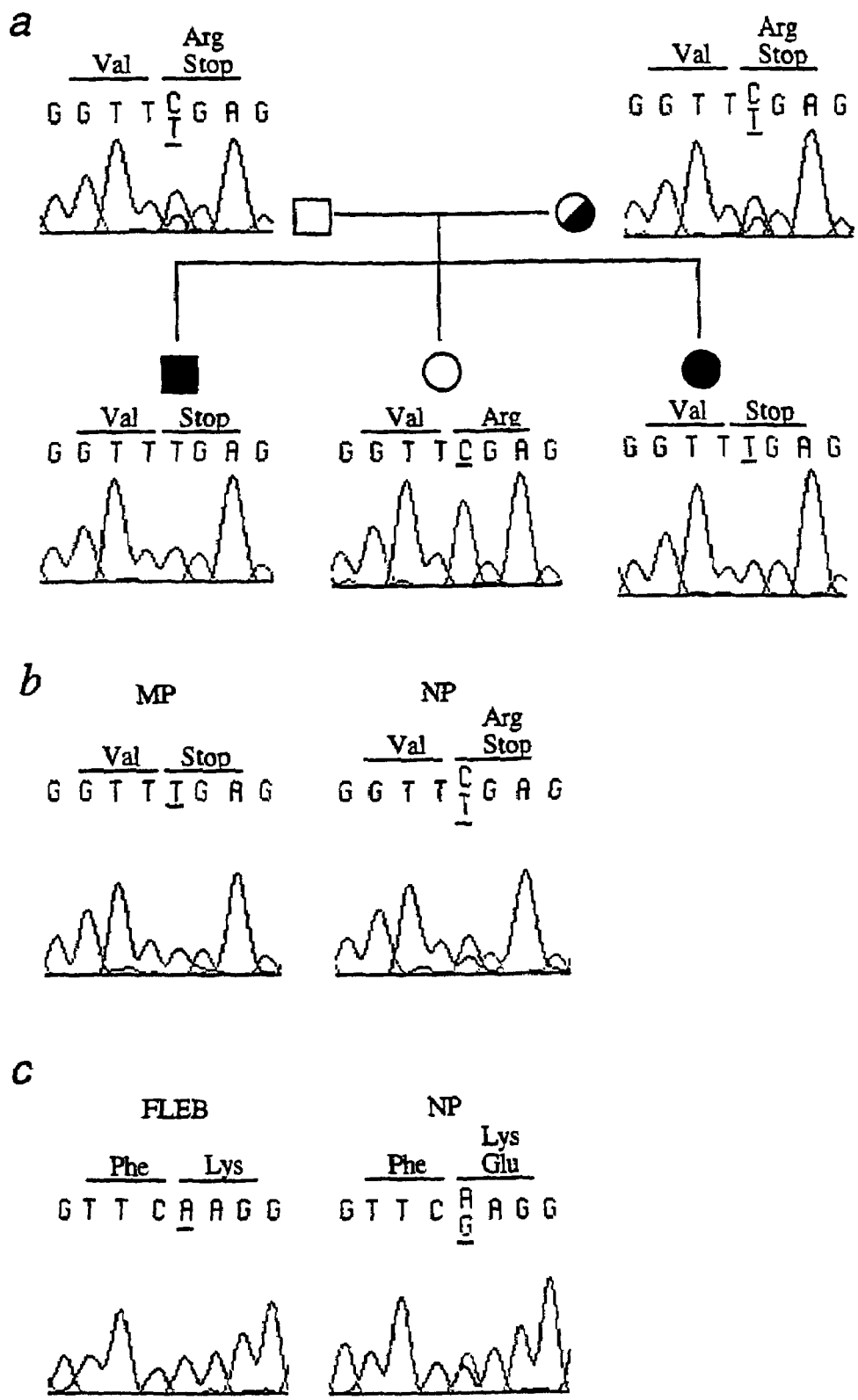
FIG. 3 shows electropherograms showing the sequence surrounding the mutations in the APECED gene. (A) Mutation analysis of a Swiss APECED family. The parents are heterozygous for the allele (normal "C" and abnormal "T"). The affected boy and girl show the "C" to "T" transition resulting in the "Arg" to "Stop" nonsense mutation at amino acid position 25 (B) Mutation analysis of two Finnish APECED patients. The patient MP is homozygous for the mutant allele (left), NP is hetrozygous for the allele (right). (C) The patient NP shows the "A" to "G" transversion resulting in the "Lys" to Glu" missense mutation at amino acid position 83. FLEB is a normal control.

The APECED gene is approximately 13-kb in length and contains 15 exons, including the exon 1' specific to AIR-2 and AIR-3. It is transcribed in the directed of centromere to telomere (FIGS. a, 2A). Based on this information, PCR primers were designed to amplify each exon from the genomic DNA and a mutation analysis of Swiss and Finnish APECED families was performed. Sequence comparison identified two mutations in the APECED gene of the patients (FIG. 3). The first mutation changes an Arg codon (CGA) to a stop codon (TGA) at amino acid position 257 in exon 6. This mutation was designated as R257stop mutation. The second mutation is a missense mutation that derived from the maternal chromosome in one Finnish patient (NP): a Lys codon (AAG) changes to a Glu codon (GAG) at amino acid 83" in exon 2. This mutation is designated as K83E mutation (FIGS. 2A, 3C).

Figure 4:
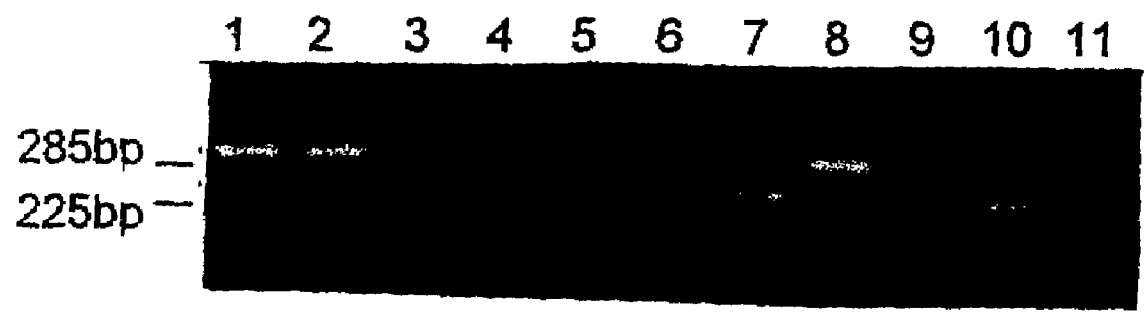
FIG. 4 shows the result of a restriction enzyme TaqI digestion assay demonstrating the R257stop mutation. Four APECED patients [HP1 (lane 1), HP2 (lane 2), NP (lane 6), and MP (lane 8)], the mothers of two families [HM (lane 5) and NM (lane 7)], two healthy siblings [HN1 (lane 3) and HN2 (lane 4)] of family H and normal controls [C1, C2 and C3 (lanes 9–11)] are shown. The APECED patients HP1, HP2 and MP are homozygotes for the R257stop mutation. The APECED patient NP is heterozygous for the R257stop mutation but is carrying a mutation at a different position in another allele of the APECED gene (shown above in FIG. 3C). Both mothers (HM and NM) and two healthy siblings (HN1 and HN2) are heterozygous for the R257stop mutation and therefore carriers of APECED but are not having the disease. Two controls (C1 and C2) are both homozygous for normal alleles. Normal alleles produce a lower 225 bp fragment, the mutated fragment is upper band at 285 bp.

The R257 stop mutation destroys a TaqI restriction enzyme site and the K83E mutation introduces a novel TaqI site. Thus these two mutations can be easily demonstrated in one or both alleles by TaqI digestion or by digestion using another enzyme cleaving at the recognition site 5'-TCGA-3' (FIG. 4).

The AIR-1 protein has strong homology in certain domains to the major autoantigens (Mi-2) associated with the autoimmune disease dermatomyositis [Seeig, H. P. et al., Arthritis Rheum. 38 (1995) 1389–1399; Ge, Q. et al., J. Clin. Invest. 96 (1995) 1730–1737], Sp140, a protein from the nuclear body, an organelle involved in the pathogenesis of certain types of leukemia, and which is also the target of antibodies in the serum of patients with the autoimmune disease primary bilary cirrhosis [Bloch, D. B. et al., J. Biol. Chem. 271 (1996) 29198–29204]. In addition, the homologies extend to other nuclear proteins such as TIF1 [Le Douarin, B. et al., EMBO J. 14 (1995) 2020–2033], LYSP100 [Dent, A. L. et al., Blood 88 (1996) 1423–1426], and putative yeast and C. elegans proteins. The AIR-1 protein homologies are principally in two PHD finger motifs (amino acid 299 to 340 and 434 to 475) (FIG. 5). AIR-1 also contains a proline-rich region (amino acid 350 to 430) (FIG. 2B). The PHD finger is a cysteine-rich structure that is distinguished from the RING finger (C3HC4) and LIM domain (C2HC5) because it contains a consensus of C4HC3. [Aasland, R. et al., Trends Biochem. Sci. 20 (1995) 56–59]. The PHD finger motif is found in a number of chromatin-associated proteins such as HRX that is involved in the t(11:17) translocation in acute leukemia [Chaplin, T. et al., Blood 86 (1995) 2073–2076]. The proline-rich region is assumed to be involved in protein—protein interaction or DNA binding. The presence of the PHD finger and proline-rich regions indicates a function for AIRs as transcription regulatory proteins. However, the AIR proteins have no apparent nuclear translocation signal, and thus other proteins containing such signal may interact with AIR to translocate it to the nucleus. In fact, the AIR proteins also have the LXXLL motif that is a signature sequence to bind to nuclear receptors [Heery, D. M. et al., Nature 387 (1997) 733–736] (FIG. 2B).

The clinical picture of APECED and the observed immunological abnormality with strong autoimmune response towards several target organs and antigens suggest that the product of the APECED gene has a central role in immune (ontogeny) maturation and regulation of immune response towards self and nonself.

According to the diagnostic method of the invention, the presence of the defective APECED gene can be detected from a biological sample by any known detection method suitable for detecting mutations. Such methods include the method described by Saiki et al. [Proc. Natl. Acad. Sci USA 86 (1989) 6230–6234) utilizing hybridization to an allele specific oligonucleotide probe, or modifications thereof; the method described by Newton, C. R. et al. [Nucl. Acids Res. 17 (1989) 2503–25161 using the DNA sequences or DNA-fragments of the invention as probes; the solid phase minisequencing method described by Syvänen et al. [Genomics 8 (1990) 684–692] in which use is made of a biotinylated probe; or the oligonucleotide ligation method described by Landegren, U. et al. [Science 241 (1988) 1077–1080]. Methods include the denaturing gradient gel electrophoresis (DGGE) [Fischer, S. G. and Lerman, L. S., PNAS 80 (1983) 1579–1583] or a modification of this method, constant denaturant gel electrophoresis (CDGE) [Hoving et al., Genes Chromosomes Cancer 5 (1992) 97–103]. The mutation separation principle of DGGE and CDGE is based on the melting behavior of the DNA double helix of a given fragment.

Since the mutations of the APECED gene involve a site sensitive to TaqI digestion, the mutation are preferably detected in one or both alleles by TaqI digestion or by digestion using another enzyme cleaving at recognition site 5'-TCGA-3' The chemical mismatch cleavage for mutation analysis can be used [Grompe, M. et al., Proc. Natl. Acad. Sci. USA 86(15)(1989) 5888–5892].

In the diagnostic method of the invention the biological sample can be any tissue or body fluid containing cells, such as blood, e.g. umbilical cord blood, separated blood cells, such as lymphocytes, B-cells, T-cells etc., biopsy material, such as fetal liver or thymus biopsy, sperm, saliva, etc. The biological sample can be, where necessary, pretreated in a suitable manner known to those skilled in the art.

When the DNA sequence of the present invention is used therapeutically any techniques presently available for gene therapy can be employed. Accordingly, in the technique known as ex vivo therapy patient cells (e.g. umbilical cord blood from the fetus) with the defective gene are taken from the patient, DNA sequences encoding the normal (healthy) gene product incorporated in a carrier vector are transducted or transfected to the cells and the cells are returned to the patient. If the techniques known as in situ therapy is used, the DNA sequences encoding the normal gene product are first inserted to a suitable carrier vector, and the carrier is then introduced to the affected tissue, such as peripheral blood, liver or bone marrow. The carrier vector used can be a retrovirus vector, an adeno virus vector, an adeno associated virus (AAV) vector or an eucaryotic vector. The therapy can be performed intra utero or during adult life. Depending on the cells to be treated these techniques lead either to a transient cure, where cells from affected organ are treated, or to a permanent cure, in case of the treatment of stem cells.

The present invention provides means for an easy and more rapid diagnosis of the diseases related to immune maturation and regulation of immune response towards self and nonself, such as APECED, and, specifically, enables prenatal diagnosis and carrier diagnosis. Furthermore, it provides a background for therapy.

The invention is now elucidated by the following non-limiting examples.

EXAMPLE 1

Localization of the APECED Gene

Genomic sequencing of cosmid DNAs was performed by the shotgun method described by Kawasaki, K. et al., Genome Res. 7 (1997) 250–261. Cosmids D1G8, D40G11, D9G11, D28B11, and D4G11 and gene marker D21S1912 are described by Kudoh, J. et al., DNA Res. 4 (1997) 45–52].

cDNA Cloning

The phage DNAs prepared from human thymus cDNA library (Clontech, HL1127a) were used as a PCR template. 20 ng of phage DNA which represents approximately $4 \times 10^8$ phages was added to a 10 ml of reaction mixture containing 1× buffer [16 mM $(NH_4)_2SO_4$, 50 mM Tris-HCl, pH 9.2, 1.75 mM $MgCl_2$, 0.001% (w/v) gelatin), 0.2 mM each of dNTPs, 1M Betaine (Sigma), 0.35 U of Tap and Pwo DNA polymerase (EXpand Long Template PCR System, Boehringer Mannheim), and 0.5 mM of each of the primers, 2F and c33R, 2F and 4R, and 2F' and 2R', respectively.

The cDNA fragment was amplified by PCR using the following conditions: 94° C. for 3 min., 35 cycles of 94° C. for 30 sec, 60° C. for 30 sec in 2F/c33R and 2F/4R or 65° C. for 30 sec in 2F/2R', and 68° C. for 90 sec. 3'- and 5'-RACE were carried out by Marathon cDNA Amplification Kit (Human Thymus; Clontech). PCR reaction was performed in a 10 µl volume containing 1× buffer (50 mM KCl, 10 mM Tris-HCl, pH 8.3, 1.5 mM $MgCl_2$, 0.001% (w/v) gelatin), 0.2 mM each of dNTPs, 0.25 U of AmpliTaq Gold polymerase (Perkin-Elmer), and 0.5 mM of each of the exon-specific primers. 3'-RACE product was amplified by PCR with the following conditions: 95° C. for 9 min., 35 cycles of 94° C. for 30 sec, 60° C. for 30 sec, and 72° C. for 30 sec.

The cDNA fragments were sequenced by the dye deoxy terminator cycle sequencing method (according to ABI PRISM Dye Terminator Cycle Sequencing Ready Reaction Kit protocol P/N 402078, Perkin Elmer Corporation, California) using specific primers, 2F and c33R, and AmpliTaq/FS DNA polymerase (Perkin-Elmer), and then analyzed by using an automatic DNA sequencer (Applied Biosystems 377). Primer sequences used were 1R: 5'-GTTCCCGAGTGGAAGGCGCTGC-3' (sequence id. no. 8)

2F: 5'-GGATTCAGACCATGTCAGCTTCA-3' (sequence id. no. 12)

3F: 5'-GAGTTCAGGTACCCAGAGATGCTG-3' (sequence id. no. 10)

c33R: 5'-CTCGCTCAGAAGGGACTCCA-3' (sequence id. no. 11)

4R: 5'-AGGGGACAGGCAGGCCAGGT-3 (sequence id. no. 9)

2F': 5'-GTGCTGTTCAAGGACTACAAC-3' (sequence id. no. 13)

2R': 5'-TGGATGAGGATCCCCTCCACG-3' (sequence id. no. 14)

AP1: 5'-CCATCCTAATACGACTCACTATAGGGC-3' (sequence id. no. 15) and c33F: 5'-GATGACACTGCCAGTCACGA-3' (sequence id. no. 7).

EXAMPLE 2

Mutation Analysis of the APECED Gene

For the mutation analysis the DNA samples were purified from periferal blood mononuclear cells from patients with APECED and from suspected carriers of APECED and from normal healthy controls (according to Sambrook et al. 1989, Molecular Cloning. A Laboratory Manual. CSH Press) and subjected to PCR using primers specific for all identified exons.

For sequencing the mutated exons, PCR fragments, 6F/6R in exon 6 and 49300F/49622R in exon 2, were amplified by PCR with the following conditions: 95° C. for 9 min., 35 cycles of 94° C. for 30 sec, 60° C. for 30 sec and 72° C. for 30 sec, and 94° C. for 3 min., 35 cycles of 94° C. for 30 sec, 60° C. for 30 sec, and 68° C. for 30 sec, respectively. The PCR products were sequenced using specific primers 6F: 5'-TGCAGGCTGTGGGAACTCCA-3' (sequence id. no. 16)

6R: 5'-AGAAAAAGAGCTGTACCCTGTG-3' (sequence id. no. 17)

3R: 5'-TGCAAGGAAGAGGGGCGTCAGC-3' (sequence id. no. 18)

49300F: 5'-TCCACCACAAGCCGAGGAGAT-3' (sequence id. no. 19) and 49622R: 5'-ACGGGCTCCTCAAA-CACCACT-3' (sequence id. no. 20).

In the mutation analysis by sequencing, two Swiss and three Finnish (HP1, HP2 and MP) patients with APECED were homozygous for R257stop allele, whereas one Finnish patient (NP) was heterozygous for this mutation (FIGS. 3A, B). The R257stop mutation of NP was derived from the paternal chromosome. The second mutation, K83E mutation, was found in one Finnish patient (NP): a Lys codon (AAG) changes to a Glu codon (GAG) at amino acid position 83 in exon 2. (FIGS. 2A, 3C). This mutation derived from the maternal chromosome.

EXAMPLE 3

Restriction Enzyme TaqI Analysis of Two Mutations in Exons 2 and 6 of APECED Gene Analysis of the mutation sites in exons 2 and 6 in large series of individuals was performed using the restriction enzyme TaqI. The TaqI digestion for exons 2 and 6 was done as follows. Ten microlitres of amplification product was incubated at 65° C. for 1 hour in 20 µl of reaction mixture containing 1× TaqI digestion buffer (New England Biolabs, NY, 100 µl/ml of BSA and 10U of TaqI enzyme (New England Biolabs, NY). After the digestion fragments were separated in 1.5% agarose gel and visualized by EtBr staining.

For exon 2, the fragment containing the mutation site K83E was amplified with primers GR1/2F and GR1/2R with the following conditions: 95° V for 3 min., 35 cycles of 94° C. for 30 sec, 62° C. for 30 sec and 72° for 1 min. The 1× reaction mix used contained 50 mM Kcl, 10 mM Tris-HCl, pH 8.3, 1.5 mM $MgCl_2$, 0.001% (w/v) gelatin), 0.2 mM each of dNTPs, 0.25 U of Dynazyme (Finnzymes, Finland), and 0.5 mM of each of the exon-specific primers. The normal allele produces a 312 bp fragment whereas the mutated allele gives a 133 bp and a 179 bp fragment. Primer sequences for GR1/2F and GR1/2R are 5'-TG-GAGATGGGCAGGCCGCAGGGTG (SEQ ID NO: 21) and 5'-CAGTCCAGCTGGGCTGAGCAGGTC (SEQ ID NO:22), respectively.

For exon 6, the fragment containing the R257stop mutation site was amplified with primers GR1/5IF and GR1/5IR with the same conditions described for exon 2 (see above). The normal allele produces a 225 bp fragment whereas the mutated allele gives a 285 bp fragment. Primer sequences for GR1/5IF and GR1/5IR are 5'-GCGGCTCCAAGAAGT-GCATCCAGG (sequence id. no. 23) and 5'-CTCCACCCT-GCAAGGAAGAGGGGC (sequence id. no. 24), respectively.

The screening of 50 Finnish and 50 Swiss healthy individuals did not reveal R257 stop or K83E mutations by TaqI digestion. Similarly, PCR analysis of 20 unaffected Japanese was performed and no mutations were found in any of these positions. These results demonstrate that the APECED gene is responsible for the pathogenesis of APECED.

Mutations were found in the AIR-1 transcript but not in the AIR-2 and AIR-3 transcripts from all the APECED patients tested. Two Swiss and three Finnish (HP1, HP2 and MP) patients who are homozygous for the R257stop mutation completely lack functional AIR-1 protein but still have intact AIR-2 and AIR-3 proteins.

One common mutation seems responsible for the genetic defect in approximately 90% of the Finnish APECED cases and a haplotype analysis with the markers D21S141, D21S1912 and PFKL shows that the R257stop mutation is likely to be this common mutation [Björses, P. et al., Am. J. Hum. Genet. 59 (1996) 879–886].

EXAMPLE 4

Analysis of the AIR Protein Expression

In this example, synthetic peptides representing amino-acid sequences of the AIR-1 protein, were used to generate a polyvalent mouse antiserum against the AIR-1 protein.

For the peptide synthesis, two peptides were chosen according to the antigenicity prediction by Pepsort program (GCC package, Wisconsin, USA). The peptides AIR-1/2 and AIR-1/6 (TLHLKEKEGCPQAFH, sequence id. no. 25 and GKNKARSSSGPKPLV, sequence id. no. 26, respectively) representing exons 2 and 6, respectively, of the APECED gene were synthesized onto a branched lysine core (Fmoc8-Lys4-Lys2-Lys-betaAla-Wang resin, Calbiochem-Novabiochem, La Jolla, Calif., USA) resulting in an octameric multible antigen peptide (MAP) [Tam, J. P. et al., Proc. Natl. Acad. Sci. USA 85 (1988) 5409–5413; Adermann, K. et al., in Solid Phase Synthesis, Biological and Biomedical Applications, pp. 429–432, Ed. R. Epton, Mayflower Worldwide Ltd., Birmingham, 1994], Syntheses were performed by Fmoc (N-(9-fluorenyl)methoxycarbonyl) chemistry on a simultaneous multiple peptide synthesizer (SMPS 350, Zinsser Analytic, Frankfurt, Germany). Purity of MAPs was analyzed by reverse-phase HPLC (System Gold, Beckman Instruments Inc, Fullerton, Calif., USA).

To obtain murine polyclonal antibodies, eight-week old Balb/c mice were immunized with an intraperitoneal injection of 25 micrograms of each peptide in 0,4 ml of a 1:1 mixture of Freund's Complete Adjuvant (Difco Laboratories, Detroit, Mich., USA) and physiological saline (NaCl, 0,15 M). One month later the animals were boosted with an intramuscular injection of 35 micrograms of antigens in Freund's incomplete adjuvant and saline (1:1) (0,2 ml were distributed into four sites). Three weeks later the peptides in a dose of 50 micrograms/mouse were administered intravenously and sera were obtained 7 days later.

For the production of EBV transformed B-cells, peripheral blood leukocytes were obtained from healthy control persons. The B-cells were transformed with EBV (Epstein-Barr virus) using standard protocol, and the cell lines were maintained in RPMI 1640, supplemented with 10% FCS (fetal calf serum). An aliquot of cells were stimulated for 12 hours with 10 mg/ml of phytohemagglutinin (PHA) to obtain mitogen-activated T-cells.

Tissue samples were obtained from stillborn fetuses at six months gestational age. Fetal liver, spleen, thymus and lymphnodes were homogenized, the homogenates were cleared with centrifugations (20 000 rpm for 20 minutes) and the samples were used for western blot analysis.

For analysis of polyclonal sera, Elisa and western blot analysis were performed. Microtitre ELISA plates (Maxisorp, Nunc, Roskilde, Denmark) were coated with the peptides (1 micrograms/well in PBS, pH 7,5) at 4° C. overnight and blocked with 2% of BSA in PBS. The plates were then incubated with titrated mouse immune sera and normal (control) sera at room temperature for 4 h. Finally the bound peptide-specific antibodies were detected by use of anti-mouse HRP-labelled immunoglobulins (Dako A/S, Denmark) essentially as previously described [Ovod, V. A. et al., AIDS 6 (1992) 25–34].

For western blotting, tissue homogenates, EBV transformed B-cells or PHA-activated T-cells were boiled for 10 minutes in 2× sample buffer (for tissue homogenates: 100 microliters of homogenate mixed with 100 microliters of sample buffer; for cells: one million cells/100 ml of buffer) and analyzed in western blotting as described in Ovod, V. A. et al., supra.

Figure 6:
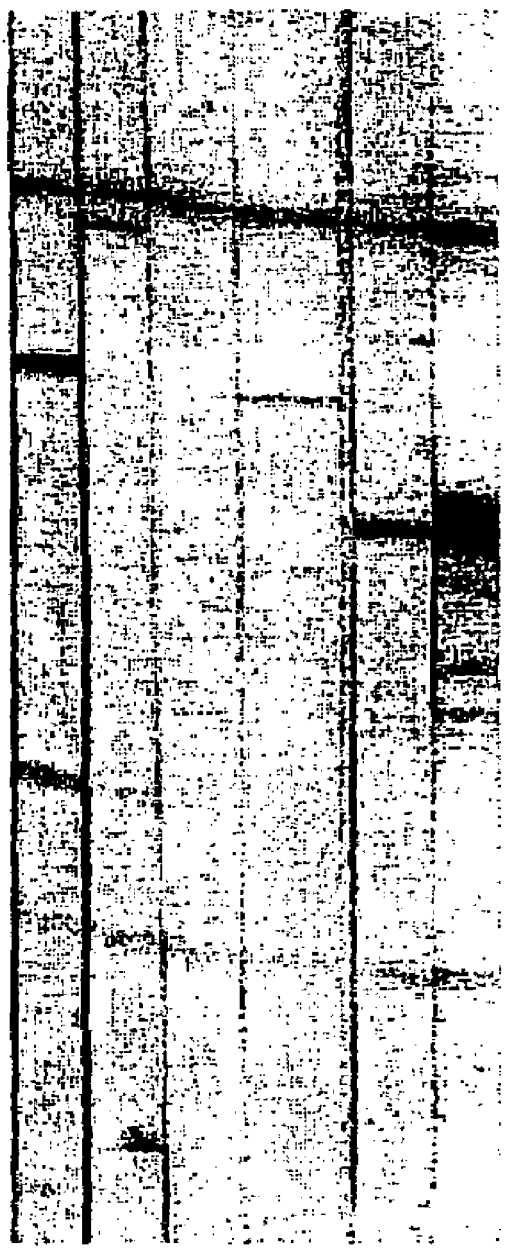
FIG. 6 is a Western blot showing the expression of AIR-1 in fetal liver. A sample of fetal liver was run on PAGE, transferred to a nitrocellulose filter and probed with sera as follows: Lane 1, control mouse serum, lane 2, control mouse serum absorbed with peptide AIR-1/2 (sequence id. no. 25), lanes 3 and 4, serum from a mouse immunized with peptide AIR-1/2 for four and six weeks, respectively and absorbed with peptide AIR-1/2, lanes 5 and 6, unabsorbed serum from a mouse immunized with peptide AIR-1/2 for four and six weeks, respectively. The strong band seen in lanes 5 and 6 represent the AIR-1 protein with a molecular weight of approx. 58 kD, the lower band is an approx. 20 kD breakdown product of the AIR protein. The bands seen in all lanes are non-specific.

The antisera so produced reacted with the AIR-1-protein low amount in normal fetal spleen, thymus and lymphonode as well as, in EBV-transformed B-cells and in PHA-activated T-cells. In the ELISA assay towards the immunogenic peptides, all four mice gave a strong reactivity towards the peptide used for the immunization. In the western blotting analysis using either the tissue homogenates or stimulated T-cells or established B-cells, a strong band of approx. 60 kD molecular weight was seen in fetal liver (FIG. 6), while weaker bands of the same size were seen in the other samples.

EXAMPLE 5

Identification of the Expression of APECED in Thymus and Other Lymphoid Organs mRNA in situ hybridization and immunohistochemistry were used to identify APECED-expressing cells in various normal fetal and adult human tissues. Thymus samples were obtained in conjunction of corrective surgery from cardiac patients aged 2–19 years. Other tissue samples were obtained from surgical biopsy or from autopsy material. This was approved by Hospital Ethics Committees at Tampere University Hospital and Helsinki University Central Hospital. The tissue materials were stored frozen or formaldehyde fixed and paraffin embedded until used.

For mRNA in situ hybridization, three cDNA fragments for riboprobes were amplified by RT-PCR from thymus mRNA (Clontech) with primer pairs: 5'-ATG GCG ACG GAC GCG GCG CTA CGC-'3 (seq. id. no. 27) and 5'-CCT GGA TGT ACT TCT TGG AGC CGC-3' (seq. id. no. 28), 5'-GAG CCC GAG GGG CCG TGG AGG GGA-3' (seq. id. no. 29) and 5'-GGC TGC ACC TCC TGG ACT GTT GCC-3' (seq. id. no. 30), and 5'-GAT CCT GCT CAG GAG ACG TGA CCC-3' (seq. id. no. 31) and 5'-CAC CAG GCA AGG AGA GGC TCC CGG-3' (seq. id. no. 32), designed to amplify fragments spanning nucleotides 137–812, 738–1185 and 1554–2009 of the sequence id. no. 1, respectively. The amplified fragments were subcloned into a pCRII-TOPO vector (Invitrogen).

For in vitro transcription the plasmids were linearized and sense and antisense probes were synthesized with digoxigenin-UTP as described (Boehringer Mannheim Nonradioactive in situ Hybridization Application Manual). Labeled probes were purified with MicroSpinG-50 columns (Pharmacia Biotech). The pretreatment and hybridization of formaldehyde fixed, paraffin embedded tissue sections were performed as described by H. Breitschopf and G. Sucharek. (Boehringer Mannheim Nonradioactive in situ Hybridization Application Manual, Detection of mRNA on paraffin embedded material of the central nervous system with DIG-labeled RNA probes, pp 136–138.)

For the preparation of antibodies to the AIR protein, the APECED cDNA (sequences 137–1774 of sequence id. no. 1) containing a full-coding region was amplified from Marathon human thymus cDNA (Clontech) with primers ExF and ExR2. The primer sequences for ExF and ExR2 were 5'-CCA CCC CAT GGC GAC GGA CG-3' (sequence id. no. 33) and 5'-GGA ATT CGG AGG GGA AGG GGG CCG CCG GA-3' (sequence id. no. 34). The amplified cDNA was digested with NcoI and EcoRI and cloned (pHPAIRE) into pET32a vector (Novagen). The protein was expressed in *E. coli* and purified by His-tag as described by manufacturer (QiaExpress Type IV Kit, Cat No 32149, Qiagen, USA).

To obtain murine polyclonal antibodies, Balb/c mice were immunised essentially as described in Example 4 using 100 micrograms of the bacterially expressed AIR protein with booster doses of 25 and 25 micrograms.

Japanese white rabbits were immunised with a synthetic peptide representing amino acids 526–545 (DGILQWAIQS-MARPAAPFPS, sequence id. no. 36) of sequence id. no. 2. The specificities of the antisera were checked with ELISA and Western blotting using standard procedures.

For immunocytochemistry, frozen sections of tissue samples were fixed for 20 min in 4% paraformaldehyde. The AIR antibody (rabbit or mouse) in an appropriate dilution was incubated for 30 min at 37° C., with a biotin conjugated anti-mouse or anti-rabbit secondary antibody (Vector, CA, USA). The biotinylated antibody was revealed by incubating with Texas Red-avidin (Vector, CA, USA) for 30 min at 37° C.

Figure 7B:
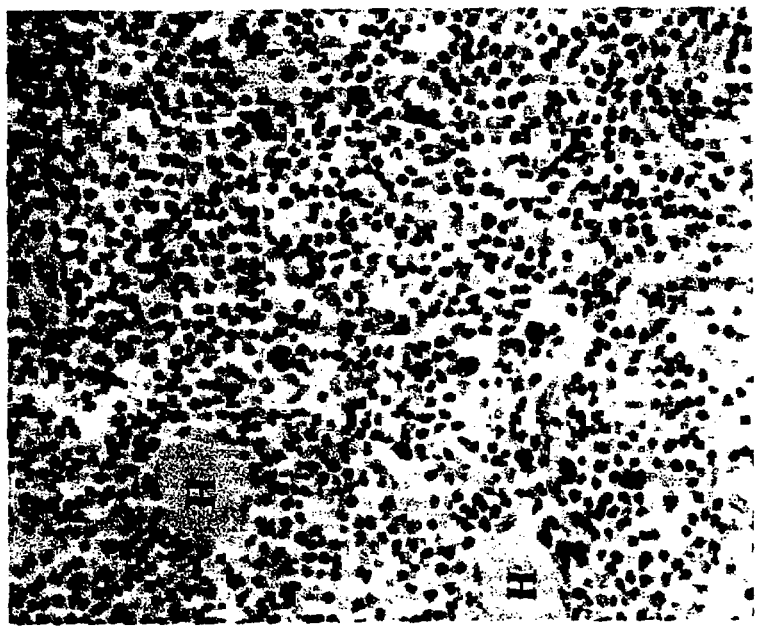
FIG. 7B shows similar cells with the same localization now stained for the AIR protein.
Figure 7A:
FIG. 7A shows APECED mRNA positive cells scattered in the medullary region of human thymus.

With in situ hybridization, a positive signal was seen in a few cells in thymus medulla (FIG. 7A). The APECED in situ-positive cells were infrequent and scattered as single cells in the medulla, but occasionally one or two APECED-expressing cells were seen adjacent to or buried into the Hassal's corpuscles that represent conglomerates of medullary epithelial cells. In the positive cells, APECED mRNA was predominantly localized in the cell nucleus. In human adult lymph node tissues, infrequent cells expressed APECED mRNA in the medulla and occasionally in the paracortical region, too (FIG. 7B) No hybridization signal was seen in the germinal centers.

Figure 7D:
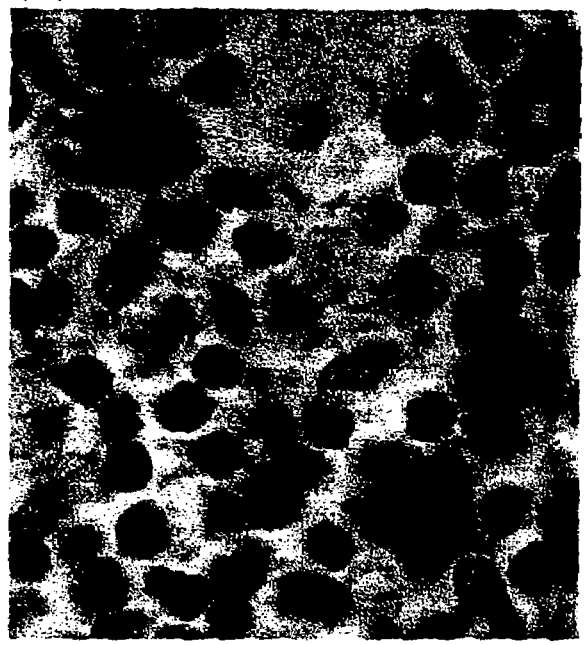
FIG. 7D shows the cytoplasmic localization of the AIR protein in a few cells in lymph node medulla.
Figure 7C:
FIG. 7C is a higher magnification of 7B, showing the localization of the AIR protein in the nuclei. Note the speckled localiation pattern in the nuclei.

Immunohistochemistry with mouse and rabbit polyclonal antisera to the AIR protein showed strong reactivity with selected cells in thymus medulla, lymph nodes and fetal liver (FIGS. 7C and 7D) The comparison of the reaction pattern obtained by immunohistochemistry to that obtained by in situ hybridization clearly established that specific, rare cells in thymus medulla and lymph node medulla and paracortex express APECED mRNA and the AIR protein. By either method, neither mRNA nor protein was detected in other adult tissues studied, including the target organs for tissue destruction in APECED (adrenal glands, parathyroid glands, gonads). In human fetal tissues, APECED positive cells were seen, although extremely infrequently, in the stroma of placental chorionic villi and in the sinusoidal area of the liver. In the fetal liver, the APECED positive cells were often localized pairwise like mirror images, suggesting that the cells were undergoing mitosis. Rare APECED expressing cells were also found in fetal thymus but the expression was not observed in other fetal tissues.

At the subcellular level, the AIR protein localized in small nuclear dots in the adult thymus, giving a characteristic speckled pattern (FIG. 7C; and FIGS. 8A and 8B), but localized in the cytoplasm of cells in lymph nodes. In the rare positive cells in fetal liver, many of which were mitotic, the AIR protein was localized in the cytoplasm.

EXAMPLE 6

Characterization of the Phenotype of the APECED Positive Cells in Thymus

Double staining with two antibodies was used to further characterize the cell type expressing APECED gene. In view of the fact that dendritic cells (DC) and thymus epithelium are both involved in the regulation of immune maturation, expression of markers for these cells were studied.

For double immunofluorescence detection the AIR staining was performed as described in example 5 with rabbit anti-AIR serum. The slides were then incubated with a second primary antibody [AE1 (Neomarkers, CA, USA), AE3 (Neomarkers, CA, USA), CD11c (Immunotech, France), or CD83 (Immunotech, France)] in an appropriate dilution for 30 min at 37° C., and the reaction was revealed by incubating with a FITC conjugated secondary anti-mouse antibody (Vector, CA, USA) for 30 min at 37° C.

Figure 8A:
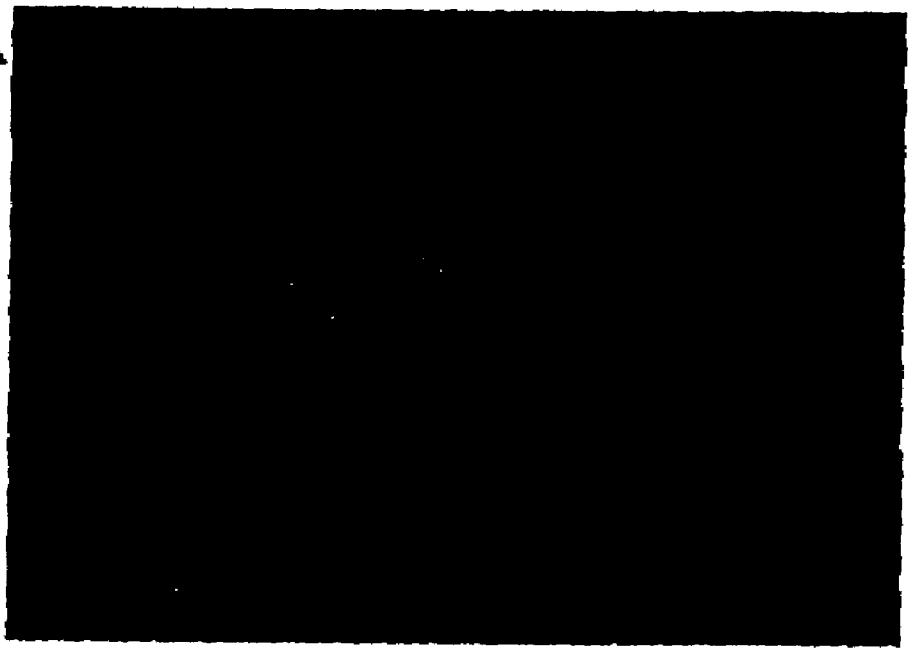
In FIG. 8A, the co-staining is with an antibody recognizing low molecular weight markers (AE1). The APECED positive cells fall into two types, one is expressing cytokeratin and is thus epithelial cell, the other one is non-epithelial and do not co-express cytokeratins.

Antibodies reacting with low molecular weight basic (AE1) or high molecular weight acidic (AE3) cytokeratins stained the thymus in a reticular fashion, and the APECED positive cells were seen either buried into this net or in close apposition with the keratin-positive cells. Confocal microscopy clearly demonstrated that some of the APECED positive cells were cytokeratin positive while some remained negative (FIG. 8A). A co-localization was stronger with AE1 than with AE3. The distribution of epithelial (AE1 positive) and non-epithelial APECED expressing cells varied but in most thymus preparates more than half were epithelial.

Figure 8B:
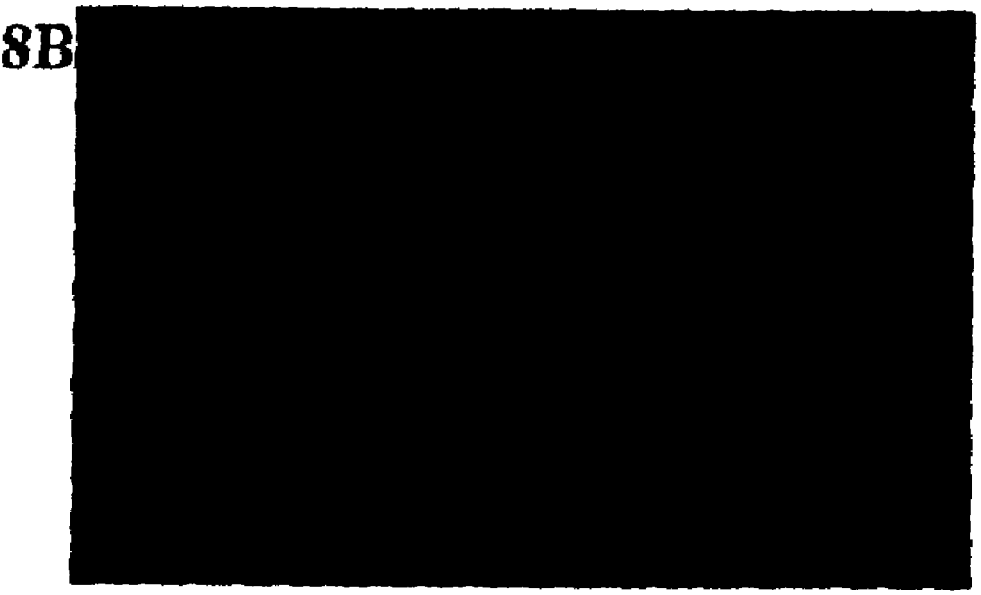
In FIG. 8B an APECED positive cell co-expresses a marker (CD83) typical for cells belonging to monocyte-macrophage-dendritic cell lineage.

Less than half of the APECED expressing cells in thymus stained with markers CD11c and CD83 that react with cells of the monocyte-macrophage-dendritic cell lineage. In most cases, the staining reaction was weak but a few cells showed an intensive staining with the given marker (FIG. 8B). CD83 costained 5 to 40% of the APECED positive cells. Antibody CD11c, reported to be specific for mature dendritic cells, reacted with up to 5–10% of the APECED positive cells. All APECED positive cells were strongly positive for HLA-DR staining, however (data not sown).

These results suggest that in thymus the APECED gene is in fact expressed in two distinct cell populations, one epithelial and the other non-epithelial. The latter cell type is likely the one also expressing the APECED gene in extrathymic lymphoid tissues.

EXAMPLE 7

APECED Expression in Stimulated Dendritic Cells In Vitro

To show an APECED expression in dendritic cells derived from peripheral blood monocytes that are DC precursors, these cells were cultured at the presence of cytokines using conditions that are known to lead to the expansion and maturation of dendritic cells.

Peripheral blood mononuclear cells were isolated by Ficoll-Hypaque centrifugation, and adherent cells were separated and cultured in the presence of human recombinant GM-CSF (1000 units/ml) and rhIL4 (1000 units/ml, both from R&D Systems), as described [Schuler, G. and Romani, N., Adv. Exp. Med. Biol. 417 (1997) 7–13]. Cells were further cultured for three days with 1/4 V/V of macrophage conditioned media. Cells were harvested at two days intervals and samples were prepared for RT-PCR. For RT-PCR total RNA was purified from DCs by using a commercial kit from Clontech (USA) (Nucleospin RNA Kit) according to manufacturer's instructions. An aliquot of RNA was transferred into cDNA with a commercial kit from Pharmacia (Sweden) (First-strand Synthesis Kit) and PCR for this DNA sample was performed. For PCR the fragment was amplified with primers 5'-GAT CCT GCT CAG GAG ACG TGA CCC-3' (seq. id. no. 31; 1554–1577 of seq. id. no. 1) and 5'-GGA CTG AGG AAG GAG GTG TCC TTC-3' (seq. id. no. 35; 1818–1841 of seq. id. no. 1) with the following conditions: 35 cycles of 95° C. for 1 min., 62° C. for 30 sec and 72° C. for 1 min. The 1× reaction mix contained 50 mM KCl, 10 mM Tris-HCl, pH8.3, 1.5 mM $MgCl_2$, 0.001% (w/v) gelatin, 0.2 mM each of dNTPs, 0.25 U of Dynazyme (Finnzymes, Finland). A fragment of 287 bp was detected by 1.5% agarose electrophoresis.

Cytospin preparations were further made for immunohistochemistry.

Figure 9:
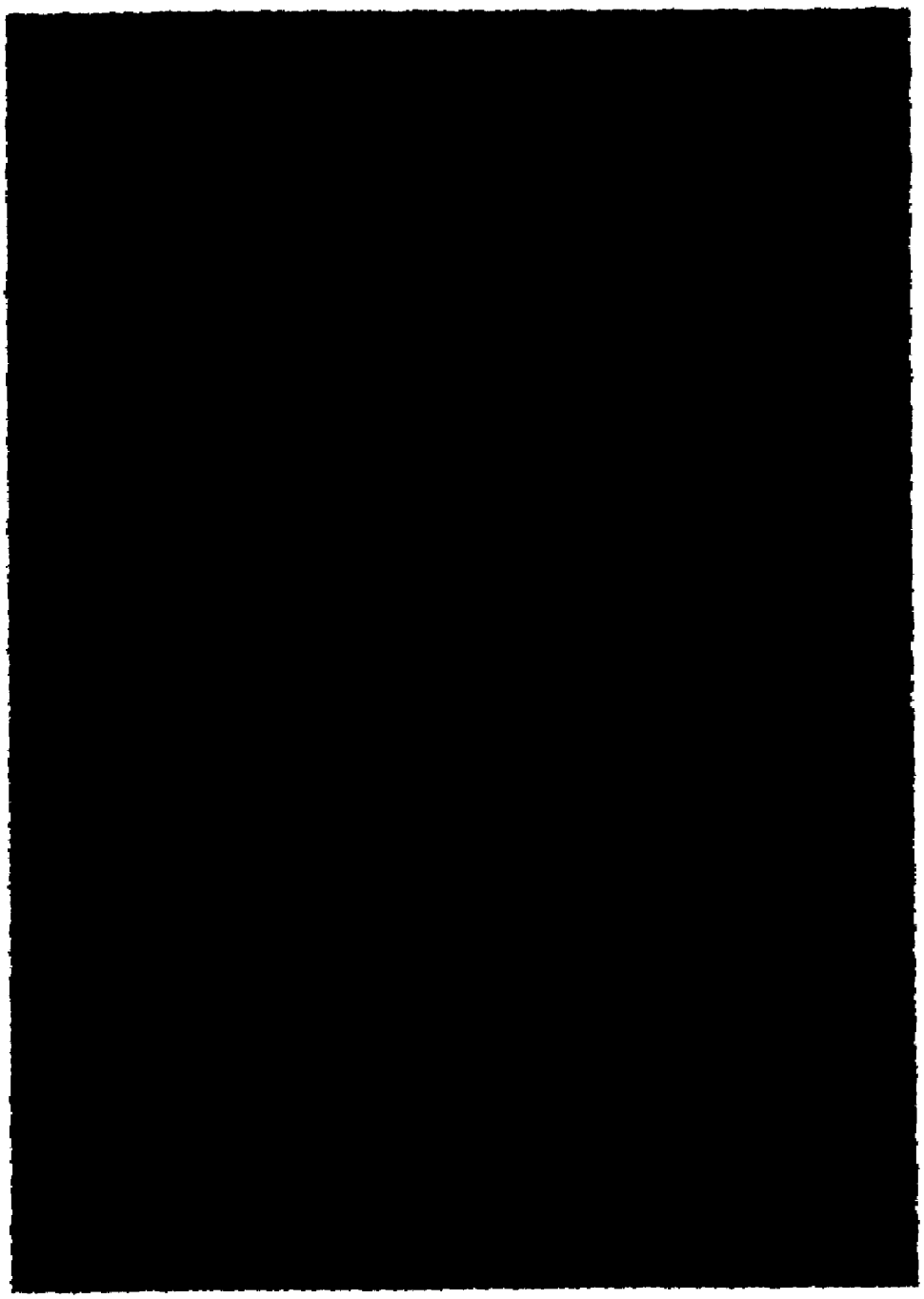
FIG. 9 shows the expression of the AIR protein, demonstrated by immunofluorescence, in mature, activated dendritic cells from peripheral blood. The expression of the AIR protein shows as distinct dots in the nuclei of dendritic cells.

During this 7 to 10 days culture period approximately half of the cells developed the characteristic veiled morphology of DC and their phenotypic cell markers (CD11c and CD83) corresponded to mature DCs (FIG. 9). The APECED expression was studied by RT-PCR and immunocytochemistry at two to three days intervals. In the starting material, i.e. the adherent cell pool from peripheral blood, no APECED expression was found. After seven days of culture in the presence of GM-CSF and IL-4, RT-PCR showed APECED mRNA expression and immunofluorescence showed a few AIR specific nuclear dots. After an additional 3-day-culture with conditioned medium from macrophage cultures a strong speckled pattern of nuclear AIR expression was seen (FIG. 9A). The RT-PCR analysis of the mature (10 days) culture confirmed the AIR protein expression.

The invention claimed is:

1. An isolated nucleic acid molecule comprising the sequence of SEQ ID NO:1.

2. An isolated nucleic acid molecule comprising SEQ ID NO:1 wherein the nucleotide at position 905 is a T instead of a C.

3. An isolated nucleic acid molecule comprising SEQ ID NO:1 wherein the nucleotide at position 383 is a G instead of an A.

* * * * *

SEQUENCE LISTING

<160> NUMBER OF SEQ ID NOS: 41

<210> SEQ ID NO 1
<211> LENGTH: 2036
<212> TYPE: DNA
<213> ORGANISM: HOMO SAPIENS
<220> FEATURE:

-continued

```
<221> NAME/KEY: CDS
<222> LOCATION: (137)..(1771)
<223> OTHER INFORMATION: /product="AIR-1"
<220> FEATURE:
<221> NAME/KEY: mat_peptide
<222> LOCATION: (1)..(545)
<223> OTHER INFORMATION: /product="AIR-1"

<400> SEQUENCE: 1
agaccgggga  cacgggcggg  cgcacagccg  gcgcggaggc  cccacagccc  cgccgggacc      60
cgaggccaag  cgaggggctg  ccagtgtccc  gggacccacc  gcgtccgccc  cagccccggg     120
tccccgcgcc cacccc atg gcg acg gac gcg gcg cta cgc cgg ctt ctg agg        172
              Met Ala Thr Asp Ala Ala Leu Arg Arg Leu Leu Arg
                1               5                   10 ctg cac cgc acg gag atc gcg gtg gcc gtg gac agc gcc ttc cca ctg            220
Leu His Arg Thr Glu Ile Ala Val Ala Val Asp Ser Ala Phe Pro Leu
            15                  20                  25 ctg cac gcg ctg gct gac cac gac gtg gtc ccc gag gac aag ttt cag            268
Leu His Ala Leu Ala Asp His Asp Val Val Pro Glu Asp Lys Phe Gln
        30                  35                  40 gag acg ctt cat ctg aag gaa aag gag ggc tgc ccc cag gcc ttc cac            316
Glu Thr Leu His Leu Lys Glu Lys Glu Gly Cys Pro Gln Ala Phe His
45                  50                  55                  60 gcc ctc ctg tcc tgg ctg ctg acc cag gac tcc aca gcc atc ctg gac            364
Ala Leu Leu Ser Trp Leu Leu Thr Gln Asp Ser Thr Ala Ile Leu Asp
                65                  70                  75 ttc tgg agg gtg ctg ttc aag gac tac aac ctg gag cgc tat ggc cgg            412
Phe Trp Arg Val Leu Phe Lys Asp Tyr Asn Leu Glu Arg Tyr Gly Arg
            80                  85                  90 ctg cag ccc atc ctg gac agc ttc ccc aaa gat gtg gac ctc agc cag            460
Leu Gln Pro Ile Leu Asp Ser Phe Pro Lys Asp Val Asp Leu Ser Gln
        95                  100                 105 ccc cgg aag ggg agg aag ccc ccg gcc gtc ccc aag gct ttg gta ccg            508
Pro Arg Lys Gly Arg Lys Pro Pro Ala Val Pro Lys Ala Leu Val Pro
    110                 115                 120 cca ccc aga ctc ccc acc aag agg aag gcc tca gaa gag gct cga gct            556
Pro Pro Arg Leu Pro Thr Lys Arg Lys Ala Ser Glu Glu Ala Arg Ala
125                 130                 135                 140 gcc gcg cca gca gcc ctg act cca agg ggc acc gcc agc cca ggc tct            604
Ala Ala Pro Ala Ala Leu Thr Pro Arg Gly Thr Ala Ser Pro Gly Ser
                145                 150                 155 caa ctg aag gcc aag ccc ccc aag aag ccg gag agc agc gca gag cag            652
Gln Leu Lys Ala Lys Pro Pro Lys Lys Pro Glu Ser Ser Ala Glu Gln
            160                 165                 170 cag cgc ctt cca ctc ggg aac ggg att cag acc atg tca gct tca gtc            700
Gln Arg Leu Pro Leu Gly Asn Gly Ile Gln Thr Met Ser Ala Ser Val
        175                 180                 185 cag aga gct gtg gcc atg tcc tcc ggg gac gtc ccg gga gcc cga ggg            748
Gln Arg Ala Val Ala Met Ser Ser Gly Asp Val Pro Gly Ala Arg Gly
    190                 195                 200 gcc gtg gag ggg atc ctc atc cag cag gtg ttt gag tca ggc ggc tcc            796
Ala Val Glu Gly Ile Leu Ile Gln Gln Val Phe Glu Ser Gly Gly Ser
205                 210                 215                 220 aag aag tgc atc cag gtt ggc ggg gag ttc tac act ccc agc aag ttc            844
Lys Lys Cys Ile Gln Val Gly Gly Glu Phe Tyr Thr Pro Ser Lys Phe
                225                 230                 235 gaa gac tcc ggc agt ggg aag aac aag gcc cgc agc agc agt ggc ccg            892
Glu Asp Ser Gly Ser Gly Lys Asn Lys Ala Arg Ser Ser Ser Gly Pro
            240                 245                 250 aag cct ctg gtt cga gcc aag gga gcc cag ggc gct gcc ccc ggt gga            940
Lys Pro Leu Val Arg Ala Lys Gly Ala Gln Gly Ala Ala Pro Gly Gly
```

-continued

| | | |
|---|---|---|
| Lys Pro Leu Val Arg Ala Lys Gly Ala Gln Gly Ala Pro Gly Gly<br>255 260 265 | | |
| ggt gag gct agg ctg ggc cag cag ggc agc gtt ccc gcc cct ctg gcc<br>Gly Glu Ala Arg Leu Gly Gln Gln Gly Ser Val Pro Ala Pro Leu Ala<br>270 275 280 | 988 | |
| ctc ccc agt gac ccc cag ctc cac cag aag aat gag gac gag tgt gcc<br>Leu Pro Ser Asp Pro Gln Leu His Gln Lys Asn Glu Asp Glu Cys Ala<br>285 290 295 300 | 1036 | |
| gtg tgt cgg gac ggc ggg gag ctc atc tgc tgt gac ggc tgc cct cgg<br>Val Cys Arg Asp Gly Gly Glu Leu Ile Cys Cys Asp Gly Cys Pro Arg<br>305 310 315 | 1084 | |
| gcc ttc cac ctg gcc tgc ctg tcc cct ccg ctc cgg gag atc ccc agt<br>Ala Phe His Leu Ala Cys Leu Ser Pro Pro Leu Arg Glu Ile Pro Ser<br>320 325 330 | 1132 | |
| ggg acc tgg agg tgc tcc agc tgc ctg cag gca aca gtc cag gag gtg<br>Gly Thr Trp Arg Cys Ser Ser Cys Leu Gln Ala Thr Val Gln Glu Val<br>335 340 345 | 1180 | |
| cag ccc cgg gca gag gag ccc cgg ccc cag gag cca ccc gtg gag acc<br>Gln Pro Arg Ala Glu Glu Pro Arg Pro Gln Glu Pro Pro Val Glu Thr<br>350 355 360 | 1228 | |
| ccg ctc ccc ccg ggg ctt agg tcg gcg gga gag gag gta aga ggt cca<br>Pro Leu Pro Pro Gly Leu Arg Ser Ala Gly Glu Glu Val Arg Gly Pro<br>365 370 375 380 | 1276 | |
| cct ggg gaa ccc cta gcc ggc atg gac acg act ctt gtc tac aag cac<br>Pro Gly Glu Pro Leu Ala Gly Met Asp Thr Thr Leu Val Tyr Lys His<br>385 390 395 | 1324 | |
| ctg ccg gct ccg cct tct gca gcc ccg ctg cca ggg ctg gac tcc tcg<br>Leu Pro Ala Pro Pro Ser Ala Ala Pro Leu Pro Gly Leu Asp Ser Ser<br>400 405 410 | 1372 | |
| gcc ctg cac ccc cta ctg tgt gtg ggt cct gag ggt cag cag aac ctg<br>Ala Leu His Pro Leu Leu Cys Val Gly Pro Glu Gly Gln Gln Asn Leu<br>415 420 425 | 1420 | |
| gct cct ggt gcg cgt tgc ggg gtg tgc gga gat ggt acg gac gtg ctg<br>Ala Pro Gly Ala Arg Cys Gly Val Cys Gly Asp Gly Thr Asp Val Leu<br>430 435 440 | 1468 | |
| cgg tgt act cac tgc gcc gct gcc ttc cac tgg cgc tgc cac ttc cca<br>Arg Cys Thr His Cys Ala Ala Ala Phe His Trp Arg Cys His Phe Pro<br>445 450 455 460 | 1516 | |
| gcc ggc acc tcc cgg ccc ggg acg ggc ctg cgc tgc aga tcc tgc tca<br>Ala Gly Thr Ser Arg Pro Gly Thr Gly Leu Arg Cys Arg Ser Cys Ser<br>465 470 475 | 1564 | |
| gga gac gtg acc cca gcc cct gtg gag ggg gtg ctg gcc ccc agc ccc<br>Gly Asp Val Thr Pro Ala Pro Val Glu Gly Val Leu Ala Pro Ser Pro<br>480 485 490 | 1612 | |
| gcc cgc ctg gcc cct ggg cct gcc aag gat gac act gcc agt cac gag<br>Ala Arg Leu Ala Pro Gly Pro Ala Lys Asp Asp Thr Ala Ser His Glu<br>495 500 505 | 1660 | |
| ccc gct ctg cac agg gat gac ctg gag tcc ctt ctg agc gag cac acc<br>Pro Ala Leu His Arg Asp Asp Leu Glu Ser Leu Leu Ser Glu His Thr<br>510 515 520 | 1708 | |
| ttc gat ggc atc ctg cag tgg gcc atc cag agc atg gcc cgt ccg gcg<br>Phe Asp Gly Ile Leu Gln Trp Ala Ile Gln Ser Met Ala Arg Pro Ala<br>525 530 535 540 | 1756 | |
| gcc ccc ttc ccc tcc tgaccccaga tggccgggac atgcagctct gatgagagag<br>Ala Pro Phe Pro Ser<br>545 | 1811 | |
| tgctgagaag gacacctcct tcctcagtcc tggaagccgg ccggctggga tcaagaaggg | 1871 | |
| gacagcgcca cctcttgtca gtgctcggct gtaaacagct ctgtgtttct ggggacacca | 1931 | |

```
gccatcatgt gcctggaaat taaaccctgc cccacttctc tactctggaa gtccccggga    1991
gcctctcctt gcctggtgac ctactaaaaa tataaaaatt agctg                   2036
```

<210> SEQ ID NO 2
<211> LENGTH: 545
<212> TYPE: PRT
<213> ORGANISM: HOMO SAPIENS

<400> SEQUENCE: 2

```
Met Ala Thr Asp Ala Ala Leu Arg Arg Leu Leu Arg Leu His Arg Thr
1               5                   10                  15

Glu Ile Ala Val Ala Val Asp Ser Ala Phe Pro Leu Leu His Ala Leu
            20                  25                  30

Ala Asp His Asp Val Val Pro Glu Asp Lys Phe Gln Glu Thr Leu His
        35                  40                  45

Leu Lys Glu Lys Glu Gly Cys Pro Gln Ala Phe His Ala Leu Leu Ser
    50                  55                  60

Trp Leu Leu Thr Gln Asp Ser Thr Ala Ile Leu Asp Phe Trp Arg Val
65                  70                  75                  80

Leu Phe Lys Asp Tyr Asn Leu Glu Arg Tyr Gly Arg Leu Gln Pro Ile
                85                  90                  95

Leu Asp Ser Phe Pro Lys Asp Val Asp Leu Ser Gln Pro Arg Lys Gly
            100                 105                 110

Arg Lys Pro Pro Ala Val Pro Lys Ala Leu Val Pro Pro Arg Leu
        115                 120                 125

Pro Thr Lys Arg Lys Ala Ser Glu Glu Ala Arg Ala Ala Pro Ala
    130                 135                 140

Ala Leu Thr Pro Arg Gly Thr Ala Ser Pro Gly Ser Gln Leu Lys Ala
145                 150                 155                 160

Lys Pro Pro Lys Lys Pro Glu Ser Ser Ala Glu Gln Arg Leu Pro
                165                 170                 175

Leu Gly Asn Gly Ile Gln Thr Met Ser Ala Ser Val Gln Arg Ala Val
            180                 185                 190

Ala Met Ser Ser Gly Asp Val Pro Gly Ala Arg Gly Ala Val Glu Gly
        195                 200                 205

Ile Leu Ile Gln Gln Val Phe Glu Ser Gly Ser Lys Lys Cys Ile
    210                 215                 220

Gln Val Gly Gly Glu Phe Tyr Thr Pro Ser Lys Phe Glu Asp Ser Gly
225                 230                 235                 240

Ser Gly Lys Asn Lys Ala Arg Ser Ser Ser Gly Pro Lys Pro Leu Val
                245                 250                 255

Arg Ala Lys Gly Ala Gln Gly Ala Ala Pro Gly Gly Glu Ala Arg
            260                 265                 270

Leu Gly Gln Gln Gly Ser Val Pro Ala Pro Leu Ala Leu Pro Ser Asp
        275                 280                 285

Pro Gln Leu His Gln Lys Asn Glu Asp Glu Cys Ala Val Cys Arg Asp
    290                 295                 300

Gly Gly Glu Leu Ile Cys Cys Asp Gly Cys Pro Arg Ala Phe His Leu
305                 310                 315                 320

Ala Cys Leu Ser Pro Pro Leu Arg Glu Ile Pro Ser Gly Thr Trp Arg
                325                 330                 335

Cys Ser Ser Cys Leu Gln Ala Thr Val Gln Glu Val Gln Pro Arg Ala
            340                 345                 350

Glu Glu Pro Arg Pro Gln Glu Pro Pro Val Glu Thr Pro Leu Pro Pro
```

```
                    355                 360                 365
Gly Leu Arg Ser Ala Gly Glu Glu Val Arg Gly Pro Pro Gly Glu Pro
        370                 375                 380

Leu Ala Gly Met Asp Thr Thr Leu Val Tyr Lys His Leu Pro Ala Pro
385                 390                 395                 400

Pro Ser Ala Ala Pro Leu Pro Gly Leu Asp Ser Ser Ala Leu His Pro
                405                 410                 415

Leu Leu Cys Val Gly Pro Glu Gly Gln Gln Asn Leu Ala Pro Gly Ala
                420                 425                 430

Arg Cys Gly Val Cys Gly Asp Gly Thr Asp Val Leu Arg Cys Thr His
            435                 440                 445

Cys Ala Ala Ala Phe His Trp Arg Cys His Phe Pro Ala Gly Thr Ser
450                 455                 460

Arg Pro Gly Thr Gly Leu Arg Cys Arg Ser Cys Ser Gly Asp Val Thr
465                 470                 475                 480

Pro Ala Pro Val Glu Gly Val Leu Ala Pro Ser Pro Ala Arg Leu Ala
                485                 490                 495

Pro Gly Pro Ala Lys Asp Asp Thr Ala Ser His Glu Pro Ala Leu His
            500                 505                 510

Arg Asp Asp Leu Glu Ser Leu Leu Ser Glu His Thr Phe Asp Gly Ile
            515                 520                 525

Leu Gln Trp Ala Ile Gln Ser Met Ala Arg Pro Ala Ala Pro Phe Pro
        530                 535                 540

Ser
545

<210> SEQ ID NO 3
<211> LENGTH: 1545
<212> TYPE: DNA
<213> ORGANISM: HOMO SAPIENS
<220> FEATURE:
<221> NAME/KEY: CDS
<222> LOCATION: (237)..(1283)
<220> FEATURE:
<221> NAME/KEY: mat peptide
<222> LOCATION: (1)..(348)
<223> OTHER INFORMATION: /product="AIR-2"

<400> SEQUENCE: 3
agagaaagtg aggtcttctc aggctcttaa gagcatggcg tttggtccag gctgtacccg      60
ctgctctcag ctgggcccgt gggtggggcg ggcgccctg ctatagccag gaggtcaagg      120
atccactggg aatgccatgc tcatctttcg tccccagcat ggtttcttaa tggggtagaa      180
gcaggtcggg agagacctcc ctgggcctgg ccccactgcc ctgtgaggaa gggttc atg      239
                                                              Met
                                                                1 tgg ttg gtg tac agt tcc ggg gcc cct gga acg cag cag cct gca aga      287
Trp Leu Val Tyr Ser Ser Gly Ala Pro Gly Thr Gln Gln Pro Ala Arg
        5                   10                  15 aac cgg gtt ttc ttc cca ata ggg atg gcc ccg ggg ggt gtc tgt tcg      335
Asn Arg Val Phe Phe Pro Ile Gly Met Ala Pro Gly Gly Val Cys Ser
            20                  25                  30 aga cca gat gga tgg gga aca ggt ggt cag ggc aga att tca ggc cct      383
Arg Pro Asp Gly Trp Gly Thr Gly Gly Gln Gly Arg Ile Ser Gly Pro
        35                  40                  45 ggc agc atg gga gca ggg cag aga ctg ggg agt tca ggt acc cag aga      431
Gly Ser Met Gly Ala Gly Gln Arg Leu Gly Ser Ser Gly Thr Gln Arg
50                  55                  60                  65
```

-continued

| | |
|---|---|
| tgc tgc tgg ggg agc tgt ttt ggg aag gag gtg gct ctc agg agg gtg<br>Cys Cys Trp Gly Ser Cys Phe Gly Lys Glu Val Ala Leu Arg Arg Val<br>              70                    75                 80 | 479 |
| ctg cac ccc agc cca gtc tgc atg ggc gtc tct tgc ctg tgc cag aag<br>Leu His Pro Ser Pro Val Cys Met Gly Val Ser Cys Leu Cys Gln Lys<br>               85                   90                 95 | 527 |
| aat gag gac gag tgt gcc gtg tgt cgg gac ggc ggg gag ctc atc tgc<br>Asn Glu Asp Glu Cys Ala Val Cys Arg Asp Gly Gly Glu Leu Ile Cys<br>        100                  105                  110 | 575 |
| tgt gac ggc tgc cct cgg gcc ttc cac ctg gcc tgc ctg tcc cct ccg<br>Cys Asp Gly Cys Pro Arg Ala Phe His Leu Ala Cys Leu Ser Pro Pro<br>115                   120                  125 | 623 |
| ctc cgg gag atc ccc agt ggg acc tgg agg tgc tcc agc tgc ctg cag<br>Leu Arg Glu Ile Pro Ser Gly Thr Trp Arg Cys Ser Ser Cys Leu Gln<br>130                   135                  140                145 | 671 |
| gca aca gtc cag gag gtg cag ccc cgg gca gag gag ccc cgg ccc cag<br>Ala Thr Val Gln Glu Val Gln Pro Arg Ala Glu Glu Pro Arg Pro Gln<br>                    150                  155                  160 | 719 |
| gag cca ccc gtg gag acc ccg ctc ccc ccg ggg ctt agg tcg gcg gga<br>Glu Pro Pro Val Glu Thr Pro Leu Pro Pro Gly Leu Arg Ser Ala Gly<br>                    165                  170                  175 | 767 |
| gag gag gta aga ggt cca cct ggg gaa ccc cta gcc ggc atg gac acg<br>Glu Glu Val Arg Gly Pro Pro Gly Glu Pro Leu Ala Gly Met Asp Thr<br>        180                  185                  190 | 815 |
| act ctt gtc tac aag cac ctg ccg gct ccg cct tct gca gcc ccg ctg<br>Thr Leu Val Tyr Lys His Leu Pro Ala Pro Pro Ser Ala Ala Pro Leu<br>               195                  200                  205 | 863 |
| cca ggt ctg gac tcc tcg gcc ctg cac ccc cta ctg tgt gtg ggt cct<br>Pro Gly Leu Asp Ser Ser Ala Leu His Pro Leu Leu Cys Val Gly Pro<br>210                   215                  220                225 | 911 |
| gag ggt cag cag aac ctg gct cct ggt gcg cgt tgc ggg gtg tgc gga<br>Glu Gly Gln Gln Asn Leu Ala Pro Gly Ala Arg Cys Gly Val Cys Gly<br>                    230                  235                  240 | 959 |
| gat ggt acg gac gtg ctg cgg tgt act cac tgc gcc gct gcc ttc cac<br>Asp Gly Thr Asp Val Leu Arg Cys Thr His Cys Ala Ala Ala Phe His<br>                  245                  250                  255 | 1007 |
| tgg cgc tgc cac ttc cca gcc ggc acc tcc cgg ccc ggg acg ggc ctg<br>Trp Arg Cys His Phe Pro Ala Gly Thr Ser Arg Pro Gly Thr Gly Leu<br>        260                  265                  270 | 1055 |
| cgc tgc aga tcc tgc tca gga gac gtg acc cca gcc cct gtg gag ggg<br>Arg Cys Arg Ser Cys Ser Gly Asp Val Thr Pro Ala Pro Val Glu Gly<br>               275                  280                  285 | 1103 |
| gtg ctg gcc ccc agc ccc gcc cgc ctg gcc cct ggg cct gcc aag gat<br>Val Leu Ala Pro Ser Pro Ala Arg Leu Ala Pro Gly Pro Ala Lys Asp<br>290                   295                  300                305 | 1151 |
| gac act gcc agt cac gag ccc gct ctg cac agg gat gac ctg gag tcc<br>Asp Thr Ala Ser His Glu Pro Ala Leu His Arg Asp Asp Leu Glu Ser<br>                    310                  315                  320 | 1199 |
| ctt ctg agc gag cac acc ttc gat ggc atc ctg cag tgg gcc atc cag<br>Leu Leu Ser Glu His Thr Phe Asp Gly Ile Leu Gln Trp Ala Ile Gln<br>               325                  330                335 | 1247 |
| agc atg gcc cgt ccg gcg gcc ccc ttc ccc tcc tga ccccagatgg<br>Ser Met Ala Arg Pro Ala Ala Pro Phe Pro Ser<br>340                   345 | 1293 |
| ccgggacatg cagctctgat gagagagtgc tgagaaggac acctccttcc tcagtcctgg | 1353 |
| aagccggccg gctgggatca agaaggggac agcgccacct cttgtcagtg ctcggctgta | 1413 |
| aacagctctg tgtttctggg gacaccagcc atcatgtgcc tggaaattaa acctgccccc | 1473 |
| acttctctac tctggaagtc cccgggagcc tctccttgcc tggtgaccta ctaaaaatat | 1533 |

```
aaaaattagc tg                                               1545
```

<210> SEQ ID NO 4
<211> LENGTH: 348
<212> TYPE: PRT
<213> ORGANISM: HOMO SAPIENS

<400> SEQUENCE: 4

```
Met Trp Leu Val Tyr Ser Ser Gly Ala Pro Gly Thr Gln Gln Pro Ala
1               5                   10                  15

Arg Asn Arg Val Phe Phe Pro Ile Gly Met Ala Pro Gly Gly Val Cys
            20                  25                  30

Ser Arg Pro Asp Gly Trp Gly Thr Gly Gly Gln Gly Arg Ile Ser Gly
        35                  40                  45

Pro Gly Ser Met Gly Ala Gly Gln Arg Leu Gly Ser Ser Gly Thr Gln
    50                  55                  60

Arg Cys Cys Trp Gly Ser Cys Phe Gly Lys Glu Val Ala Leu Arg Arg
65                  70                  75                  80

Val Leu His Pro Ser Pro Val Cys Met Gly Val Ser Cys Leu Cys Gln
                85                  90                  95

Lys Asn Glu Asp Glu Cys Ala Val Cys Arg Asp Gly Gly Glu Leu Ile
            100                 105                 110

Cys Cys Asp Gly Cys Pro Arg Ala Phe His Leu Ala Cys Leu Ser Pro
        115                 120                 125

Pro Leu Arg Glu Ile Pro Ser Gly Thr Trp Arg Cys Ser Ser Cys Leu
    130                 135                 140

Gln Ala Thr Val Gln Glu Val Gln Pro Arg Ala Glu Glu Pro Arg Pro
145                 150                 155                 160

Gln Glu Pro Pro Val Glu Thr Pro Leu Pro Pro Gly Leu Arg Ser Ala
                165                 170                 175

Gly Glu Glu Val Arg Gly Pro Pro Glu Pro Leu Ala Gly Met Asp
            180                 185                 190

Thr Thr Leu Val Tyr Lys His Leu Pro Ala Pro Ser Ala Ala Pro
        195                 200                 205

Leu Pro Gly Leu Asp Ser Ser Ala Leu His Pro Leu Cys Val Gly
    210                 215                 220

Pro Glu Gly Gln Gln Asn Leu Ala Pro Gly Ala Arg Cys Gly Val Cys
225                 230                 235                 240

Gly Asp Gly Thr Asp Val Leu Arg Cys Thr His Cys Ala Ala Ala Phe
                245                 250                 255

His Trp Arg Cys His Phe Pro Ala Gly Thr Ser Arg Pro Gly Thr Gly
            260                 265                 270

Leu Arg Cys Arg Ser Cys Ser Gly Asp Val Thr Pro Ala Pro Val Glu
        275                 280                 285

Gly Val Leu Ala Pro Ser Pro Ala Arg Leu Ala Pro Gly Pro Ala Lys
    290                 295                 300

Asp Asp Thr Ala Ser His Glu Pro Ala Leu His Arg Asp Asp Leu Glu
305                 310                 315                 320

Ser Leu Leu Ser Glu His Thr Phe Asp Gly Ile Leu Gln Trp Ala Ile
                325                 330                 335

Gln Ser Met Ala Arg Pro Ala Ala Pro Phe Pro Ser
            340                 345
```

<210> SEQ ID NO 5

-continued

```
<211> LENGTH: 1463
<212> TYPE: DNA
<213> ORGANISM: HOMO SAPIENS
<220> FEATURE:
<221> NAME/KEY: CDS
<222> LOCATION: (237)..(1001)
<223> OTHER INFORMATION: /product=:AIR-3"
<220> FEATURE:
<221> NAME/KEY: mat peptide
<222> LOCATION: (1)..(254)
<223> OTHER INFORMATION: /product="AIR-3"

<400> SEQUENCE: 5
agagaaagtg aggtcttctc aggctcttaa gagcatggcg tttggtccag gctgtacccg    60
ctgctctcag ctgggcccgt gggtgggccg ggcgccctg ctatagccag gaggtcaagg    120
atccactggg aatgccatgc tcatctttcg tccccagcat ggtttcttaa tggggtagaa    180
gcaggtcggg agagacctcc ctgggcctgg ccccactgcc ctgtgaggaa gggttc atg    239
                                                                Met
                                                                  1 tgg ttg gtg tac agt tcc ggg gcc cct gga acg cag cag cct gca aga    287
Trp Leu Val Tyr Ser Ser Gly Ala Pro Gly Thr Gln Gln Pro Ala Arg
          5                  10                  15 aac cgg gtt ttc ttc cca ata ggg atg gcc ccg ggg ggt gtc tgt tgg    335
Asn Arg Val Phe Phe Pro Ile Gly Met Ala Pro Gly Gly Val Cys Trp
         20                  25                  30 aga cca gat gga tgg gga aca ggt ggt cag ggc aga att tca ggc cct    383
Arg Pro Asp Gly Trp Gly Thr Gly Gly Gln Gly Arg Ile Ser Gly Pro
     35                  40                  45 ggc agc atg gga gca ggg cag aga ctg ggg agt tca ggt acc cag aga    431
Gly Ser Met Gly Ala Gly Gln Arg Leu Gly Ser Ser Gly Thr Gln Arg
 50                  55                  60                  65 tgc tgc tgg ggg agc tgt ttt ggg aag gag gtg gct ctc agg agg gtg    479
Cys Cys Trp Gly Ser Cys Phe Gly Lys Glu Val Ala Leu Arg Arg Val
                 70                  75                  80 ctg cac ccc agc cca gtc tgc atg ggc gtc tct tgc ctg tgc cag aag    527
Leu His Pro Ser Pro Val Cys Met Gly Val Ser Cys Leu Cys Gln Lys
             85                  90                  95 aat gag gac gag tgt gcc gtg tgt cgg gac ggc ggg gag ctc atc tgc    575
Asn Glu Asp Glu Cys Ala Val Cys Arg Asp Gly Gly Glu Leu Ile Cys
        100                 105                 110 tgt gac ggc tgc cct cgg gcc ttc cac ctg gcc tgc ctg tcc cct ccg    623
Cys Asp Gly Cys Pro Arg Ala Phe His Leu Ala Cys Leu Ser Pro Pro
    115                 120                 125 ctc cgg gag atc ccc agt ggg acc tgg agg tgc tcc agc tgc ctg cag    671
Leu Arg Glu Ile Pro Ser Gly Thr Trp Arg Cys Ser Ser Cys Leu Gln
130                 135                 140                 145 gca aca gtc cag gag gtg cag ccc cgg gca gag gag ccc cgg ccc cag    719
Ala Thr Val Gln Glu Val Gln Pro Arg Ala Glu Glu Pro Arg Pro Gln
                150                 155                 160 gag cca ccc gtg gag acc ccg ctc ccc ccg ggg ctt agg tcg gcg gga    767
Glu Pro Pro Val Glu Thr Pro Leu Pro Pro Gly Leu Arg Ser Ala Gly
            165                 170                 175 gag gag ccc cgc tgc cag ggc tgg act cct cgg ccc tgc acc ccc tac    815
Glu Glu Pro Arg Cys Gln Gly Trp Thr Pro Arg Pro Cys Thr Pro Tyr
        180                 185                 190 tgt gtg tgg gtc ctg agg gtc agc aga acc tgg ctc ctg gtg cgc gtt    863
Cys Val Trp Val Leu Arg Val Ser Arg Thr Trp Leu Leu Val Arg Val
    195                 200                 205 gcg ggg tgt gcg gag atg gta cgg acg tgc tgc ggt gta ctc act gcg    911
Ala Gly Cys Ala Glu Met Val Arg Thr Cys Cys Gly Val Leu Thr Ala
210                 215                 220                 225
```

-continued

```
ccg ctg cct tcc act ggc gct gcc act tcc cag ccg gca cct ccc ggc     959
Pro Leu Pro Ser Thr Gly Ala Ala Thr Ser Gln Pro Ala Pro Pro Gly
            230                 235                 240 ccg gga cgg gcc tgc gct gca gat cct gct cag gag acg tga            1001
Pro Gly Arg Ala Cys Ala Ala Asp Pro Ala Gln Glu Thr
            245                 250 ccccagcccc tgtggagggg gtgctggccc cagccccgc cgcctggcc cctgggcctg    1061
ccaaggatga cactgccagt cacgagcccg ctctgcacag ggatgacctg gagtcccttc  1121
tgagcgagca ccttcgat ggcatcctgc agtgggccat ccagagcatg gcccgtccgg    1181
cggccccctt ccctcctga ccccagatgg ccgggacatg cagctctgat gagagagtgc   1241
tgagaaggac acctccttcc tcagtcctgg aagccggccg gctgggatca agaaggggac  1301
agcgccacct cttgtcagtg ctcggctgta acagctctg tgtttctggg gacaccagcc   1361
atcatgtgcc tggaaattaa accctgcccc acttctctac tctggaagtc cccgggagcc  1421
tctccttgcc tggtgaccta ctaaaaatat aaaaattagc tg                     1463
```

<210> SEQ ID NO 6
<211> LENGTH: 254
<212> TYPE: PRT
<213> ORGANISM: HOMO SAPIENS

<400> SEQUENCE: 6

```
Met Trp Leu Val Tyr Ser Ser Gly Ala Pro Gly Thr Gln Gln Pro Ala
1               5                   10                  15

Arg Asn Arg Val Phe Phe Pro Ile Gly Met Ala Pro Gly Gly Val Cys
            20                  25                  30

Trp Arg Pro Asp Gly Trp Thr Gly Gly Gln Gly Arg Ile Ser Gly
        35                  40                  45

Pro Gly Ser Met Gly Ala Gly Gln Arg Leu Gly Ser Ser Gly Thr Gln
    50                  55                  60

Arg Cys Cys Trp Gly Ser Cys Phe Gly Lys Glu Val Ala Leu Arg Arg
65                  70                  75                  80

Val Leu His Pro Ser Pro Val Cys Met Gly Val Ser Cys Leu Cys Gln
                85                  90                  95

Lys Asn Glu Asp Glu Cys Ala Val Cys Arg Asp Gly Gly Glu Leu Ile
            100                 105                 110

Cys Cys Asp Gly Cys Pro Arg Ala Phe His Leu Ala Cys Leu Ser Pro
        115                 120                 125

Pro Leu Arg Glu Ile Pro Ser Gly Thr Trp Arg Cys Ser Ser Cys Leu
    130                 135                 140

Gln Ala Thr Val Gln Glu Val Gln Pro Arg Ala Glu Glu Pro Arg Pro
145                 150                 155                 160

Gln Glu Pro Pro Val Glu Thr Pro Leu Pro Pro Gly Leu Arg Ser Ala
                165                 170                 175

Gly Glu Glu Pro Arg Cys Gln Gly Trp Thr Pro Arg Pro Cys Thr Pro
            180                 185                 190

Tyr Cys Val Trp Val Leu Arg Val Ser Arg Thr Trp Leu Leu Val Arg
        195                 200                 205

Val Ala Gly Cys Ala Glu Met Val Arg Thr Cys Cys Gly Val Leu Thr
    210                 215                 220

Ala Pro Leu Pro Ser Thr Gly Ala Ala Thr Ser Gln Pro Ala Pro Pro
225                 230                 235                 240

Gly Pro Gly Arg Ala Cys Ala Ala Asp Pro Ala Gln Glu Thr
```

<210> SEQ ID NO 7
<211> LENGTH: 20
<212> TYPE: DNA
<213> ORGANISM: ARTIFICIAL
<220> FEATURE:
<223> OTHER INFORMATION: Description of Artificial Sequence: PRIMER

<400> SEQUENCE: 7
gatgacactg ccagtcacga        20

<210> SEQ ID NO 8
<211> LENGTH: 22
<212> TYPE: DNA
<213> ORGANISM: ARTIFICIAL
<220> FEATURE:
<223> OTHER INFORMATION: Description of Artificial Sequence: PRIMER

<400> SEQUENCE: 8
gttcccgagt ggaaggcgct gc        22

<210> SEQ ID NO 9
<211> LENGTH: 20
<212> TYPE: DNA
<213> ORGANISM: ARTIFICIAL
<220> FEATURE:
<223> OTHER INFORMATION: Description of Artificial Sequence: PRIMER

<400> SEQUENCE: 9
aggggacagg caggccaggt        20

<210> SEQ ID NO 10
<211> LENGTH: 24
<212> TYPE: DNA
<213> ORGANISM: ARTIFICIAL
<220> FEATURE:
<223> OTHER INFORMATION: Description of Artificial Sequence: PRIMER

<400> SEQUENCE: 10
gagttcaggt acccagagat gctg        24

<210> SEQ ID NO 11
<211> LENGTH: 20
<212> TYPE: DNA
<213> ORGANISM: ARTIFICIAL
<220> FEATURE:
<223> OTHER INFORMATION: Description of Artificial Sequence: PRIMER

<400> SEQUENCE: 11
ctcgctcaga agggactcca        20

<210> SEQ ID NO 12
<211> LENGTH: 23
<212> TYPE: DNA
<213> ORGANISM: ARTIFICIAL
<220> FEATURE:
<223> OTHER INFORMATION: Description of Artificial Sequence: PRIMER

<400> SEQUENCE: 12
ggattcagac catgtcagct tca        23

<210> SEQ ID NO 13
<211> LENGTH: 21
<212> TYPE: DNA
<213> ORGANISM: ARTIFICIAL

```
<220> FEATURE:
<223> OTHER INFORMATION: Description of Artificial Sequence: PRIMER

<400> SEQUENCE: 13
gtgctgttca aggatcacaa c                                              21

<210> SEQ ID NO 14
<211> LENGTH: 21
<212> TYPE: DNA
<213> ORGANISM: ARTIFICIAL
<220> FEATURE:
<223> OTHER INFORMATION: Description of Artificial Sequence: PRIMER

<400> SEQUENCE: 14
tggatgagga tcccctccac g                                              21

<210> SEQ ID NO 15
<211> LENGTH: 27
<212> TYPE: DNA
<213> ORGANISM: ARTIFICIAL
<220> FEATURE:
<223> OTHER INFORMATION: Description of Artificial Sequence: PRIMER

<400> SEQUENCE: 15
ccatcctaat acgactcact atagggc                                        27

<210> SEQ ID NO 16
<211> LENGTH: 20
<212> TYPE: DNA
<213> ORGANISM: ARTIFICIAL
<220> FEATURE:
<223> OTHER INFORMATION: Description of Artificial Sequence: PRIMER

<400> SEQUENCE: 16
tgcaggctgt gggaactcca                                                20

<210> SEQ ID NO 17
<211> LENGTH: 22
<212> TYPE: DNA
<213> ORGANISM: ARTIFICIAL
<220> FEATURE:
<223> OTHER INFORMATION: Description of Artificial Sequence: PRIMER

<400> SEQUENCE: 17
agaaaaagag ctgtaccctg tg                                             22

<210> SEQ ID NO 18
<211> LENGTH: 22
<212> TYPE: DNA
<213> ORGANISM: ARTIFICIAL
<220> FEATURE:
<223> OTHER INFORMATION: Description of Artificial Sequence: PRIMER

<400> SEQUENCE: 18
tgcaaggaag agggggcgtca gc                                            22

<210> SEQ ID NO 19
<211> LENGTH: 21
<212> TYPE: DNA
<213> ORGANISM: ARTIFICIAL
<220> FEATURE:
<223> OTHER INFORMATION: Description of Artificial Sequence: PRIMER

<400> SEQUENCE: 19
tccaccacaa gccgaggaga t                                              21
```

<210> SEQ ID NO 20
<211> LENGTH: 21
<212> TYPE: DNA
<213> ORGANISM: ARTIFICIAL
<220> FEATURE:
<223> OTHER INFORMATION: Description of Artificial Sequence: PRIMER

<400> SEQUENCE: 20
acgggctcct caaacaccac t                                        21

<210> SEQ ID NO 21
<211> LENGTH: 24
<212> TYPE: DNA
<213> ORGANISM: ARTIFICIAL
<220> FEATURE:
<223> OTHER INFORMATION: Description of Artificial Sequence: PRIMER

<400> SEQUENCE: 21
tggagatggg caggccgcag ggtg                                     24

<210> SEQ ID NO 22
<211> LENGTH: 24
<212> TYPE: DNA
<213> ORGANISM: ARTIFICIAL
<220> FEATURE:
<223> OTHER INFORMATION: Description of Artificial Sequence: PRIMER

<400> SEQUENCE: 22
cagtccagct gggctgagca ggtg                                     24

<210> SEQ ID NO 23
<211> LENGTH: 24
<212> TYPE: DNA
<213> ORGANISM: ARTIFICIAL
<220> FEATURE:
<223> OTHER INFORMATION: Description of Artificial Sequence: PRIMER

<400> SEQUENCE: 23
gcggctccaa gaagtgcatc cagg                                     24

<210> SEQ ID NO 24
<211> LENGTH: 24
<212> TYPE: DNA
<213> ORGANISM: ARTIFICIAL
<220> FEATURE:
<223> OTHER INFORMATION: Description of Artificial Sequence: PRIMER

<400> SEQUENCE: 24
ctccaccctg caaggaagag gggc                                     24

<210> SEQ ID NO 25
<211> LENGTH: 16
<212> TYPE: PRT
<213> ORGANISM: ARTIFICIAL
<220> FEATURE:
<223> OTHER INFORMATION: Description of Artificial Sequence: PRIMER

<400> SEQUENCE: 25

Thr Leu His Leu Lys Glu Lys Glu Gly Cys Pro Val Gln Ala Phe His
1               5                   10                  15

<210> SEQ ID NO 26
<211> LENGTH: 15
<212> TYPE: PRT
<213> ORGANISM: ARTIFICIAL
<220> FEATURE:

<223> OTHER INFORMATION: Description of Artificial Sequence: PRIMER

<400> SEQUENCE: 26

Cys Lys Asn Lys Ala Arg Ser Ser Ser Gly Pro Lys Pro Leu Val
1               5                   10                  15

<210> SEQ ID NO 27
<211> LENGTH: 24
<212> TYPE: DNA
<213> ORGANISM: ARTIFICIAL
<220> FEATURE:
<223> OTHER INFORMATION: Description of Artificial Sequence: PRIMER

<400> SEQUENCE: 27
atggcgacgg acgcggcgct acgc                                      24

<210> SEQ ID NO 28
<211> LENGTH: 24
<212> TYPE: DNA
<213> ORGANISM: ARTIFICIAL
<220> FEATURE:
<223> OTHER INFORMATION: Description of Artificial Sequence: PRIMER

<400> SEQUENCE: 28
cctggatgta cttcttggag ccgc                                      24

<210> SEQ ID NO 29
<211> LENGTH: 24
<212> TYPE: DNA
<213> ORGANISM: ARTIFICIAL
<220> FEATURE:
<223> OTHER INFORMATION: Description of Artificial Sequence: PRIMER

<400> SEQUENCE: 29
gagcccgagg ggccgtggag ggga                                      24

<210> SEQ ID NO 30
<211> LENGTH: 24
<212> TYPE: DNA
<213> ORGANISM: ARTIFICIAL
<220> FEATURE:
<223> OTHER INFORMATION: Description of Artificial Sequence: PRIMER

<400> SEQUENCE: 30
ggctgcacct cctggactgt tgcc                                      24

<210> SEQ ID NO 31
<211> LENGTH: 24
<212> TYPE: DNA
<213> ORGANISM: ARTIFICIAL
<220> FEATURE:
<223> OTHER INFORMATION: Description of Artificial Sequence: PRIMER

<400> SEQUENCE: 31
gatcctgctc aggagacgtg accc                                      24

<210> SEQ ID NO 32
<211> LENGTH: 24
<212> TYPE: DNA
<213> ORGANISM: ARTIFICIAL
<220> FEATURE:
<223> OTHER INFORMATION: Description of Artificial Sequence: PRIMER

<400> SEQUENCE: 32
caccaggcaa ggagaggctc ccgg                                      24

<210> SEQ ID NO 33
<211> LENGTH: 20
<212> TYPE: DNA
<213> ORGANISM: ARTIFICIAL
<220> FEATURE:
<223> OTHER INFORMATION: Description of Artificial Sequence: PRIMER

<400> SEQUENCE: 33
ccaccccatg gcgacggacg                                              20

<210> SEQ ID NO 34
<211> LENGTH: 29
<212> TYPE: DNA
<213> ORGANISM: ARTIFICIAL
<220> FEATURE:
<223> OTHER INFORMATION: Description of Artificial Sequence: PRIMER

<400> SEQUENCE: 34
ggaattcgga ggggaagggg gccgccgga                                    29

<210> SEQ ID NO 35
<211> LENGTH: 24
<212> TYPE: DNA
<213> ORGANISM: ARTIFICIAL
<220> FEATURE:
<223> OTHER INFORMATION: Description of Artificial Sequence: PRIMER

<400> SEQUENCE: 35
ggactgagga aggaggtgtc cttc                                         24

<210> SEQ ID NO 36
<211> LENGTH: 20
<212> TYPE: PRT
<213> ORGANISM: ARTIFICIAL
<220> FEATURE:
<223> OTHER INFORMATION: Description of Artificial Sequence:  PRIMER

<400> SEQUENCE: 36

Asp Gly Ile Leu Gln Trp Ala Ile Gln Ser Met Ala Arg Pro Ala Ala
1               5                   10                  15

Pro Phe Pro Ser
            20

<210> SEQ ID NO 37
<211> LENGTH: 42
<212> TYPE: PRT
<213> ORGANISM: Homo sapiens

<400> SEQUENCE: 37

Cys Ala Val Cys Arg Asp Gly Gly Glu Leu Ile Cys Cys Asp Gly Cys
1               5                   10                  15

Pro Arg Ala Phe His Leu Ala Cys Leu Ser Pro Pro Leu Arg Glu Ile
            20                  25                  30

Pro Ser Gly Thr Trp Arg Cys Ser Ser Cys
        35                  40

<210> SEQ ID NO 38
<211> LENGTH: 42
<212> TYPE: PRT
<213> ORGANISM: HOMO SAPIENS

<400> SEQUENCE: 38

Cys Gly Val Cys Gly Asp Gly Thr Asp Val Leu Arg Cys Thr His Cys
1               5                   10                  15

```
Ala Ala Ala Phe His Trp Arg Cys His Phe Pro Ala Gly Thr Ser Arg
            20                  25                  30

Pro Gly Thr Gly Leu Arg Cys Arg Ser Cys
        35                  40

<210> SEQ ID NO 39
<211> LENGTH: 42
<212> TYPE: PRT
<213> ORGANISM: HOMO SAPIENS

<400> SEQUENCE: 39

Cys Glu Val Cys Gln Gln Gly Gly Glu Ile Ile Leu Cys Asp Thr Cys
1               5                   10                  15

Pro Arg Ala Thr His Met Val Cys Leu Asp Pro Asp Met Glu Lys Ala
            20                  25                  30

Pro Glu Gly Leu Trp Ser Cys Pro His Cys
        35                  40

<210> SEQ ID NO 40
<211> LENGTH: 42
<212> TYPE: PRT
<213> ORGANISM: HOMO SAPIENS

<400> SEQUENCE: 40

Cys Arg Val Cys Lys Asp Gly Gly Glu Leu Ile Cys Cys Asp Thr Cys
1               5                   10                  15

Pro Ser Ser Tyr His Ile His Cys Leu Asn Pro Pro Leu Pro Glu Ile
            20                  25                  30

Pro Asn Gly Glu Trp Leu Cys Pro Arg Cys
        35                  40

<210> SEQ ID NO 41
<211> LENGTH: 42
<212> TYPE: PRT
<213> ORGANISM: HOMO SAPIENS

<400> SEQUENCE: 41

Cys Ala Val Cys Gln Asn Gly Gly Glu Leu Ile Cys Cys Glu Lys Cys
1               5                   10                  15

Pro Lys Val Phe His Leu Ser Cys His Val Pro Thr Leu Thr Asn Phe
            20                  25                  30

Pro Ser Gly Glu Trp Ile Cys Thr Phe Cys
        35                  40
```